US010987325B2

(12) United States Patent
Bradley et al.

(10) Patent No.: US 10,987,325 B2
(45) Date of Patent: Apr. 27, 2021

(54) COMPOSITIONS AND USES THEREOF FOR TREATING INFLAMMATORY DISEASES AND PROBIOTIC COMPOSITIONS

(71) Applicant: CHAIN Biotechnology Limited, Oxfordshire (GB)

(72) Inventors: Benjamin Bradley, Greater London (GB); Edward Green, Greater London (GB); Daniela Heeg, Greater London (GB)

(73) Assignee: CHAIN Biotechnology Limited, Oxfordshire (GB)

( * ) Notice: Subject to any disclaimer, the term of this patent is extended or adjusted under 35 U.S.C. 154(b) by 223 days.

(21) Appl. No.: 16/334,966

(22) PCT Filed: Sep. 21, 2017

(86) PCT No.: PCT/GB2017/052832
§ 371 (c)(1),
(2) Date: Mar. 20, 2019

(87) PCT Pub. No.: WO2018/055388
PCT Pub. Date: Mar. 29, 2018

(65) Prior Publication Data

US 2020/0030266 A1 Jan. 30, 2020

(30) Foreign Application Priority Data

Sep. 21, 2016 (GB) ..................................... 1616058
Apr. 27, 2017 (GB) ..................................... 1706751

(51) Int. Cl.
*A23L 33/135* (2016.01)
*A61K 35/74* (2015.01)
(Continued)

(52) U.S. Cl.
CPC .............. *A61K 31/19* (2013.01); *A23K 10/18* (2016.05); *A23L 33/135* (2016.08);
(Continued)

(58) Field of Classification Search
CPC ... A23K 10/18; A23L 33/135; A23V 2002/00; A61K 2035/115; A61K 31/19;
(Continued)

(56) References Cited

U.S. PATENT DOCUMENTS 4,211,846 A * 7/1980 Lafferty .................. C07C 59/01 435/141
6,207,856 B1 3/2001 Veech
2003/0203459 A1* 10/2003 Chen ......................... C12P 7/42 435/136

FOREIGN PATENT DOCUMENTS

CN 102559550 A 7/2012
EP 1661574 A1 5/2006
(Continued)

OTHER PUBLICATIONS

Amiot, A., et al., "Current, new and future biological agents on the horizon for the treatment of inflammatory bowel diseases," *Therapeutic Advances in Gastroenterology* (2015), 8 (2): p. 66-82.
(Continued)

*Primary Examiner* — Ernst V Arnold
(74) *Attorney, Agent, or Firm* — Cooley LLP

(57) ABSTRACT

The invention relates to compositions and uses thereof in methods for treating an inflammatory disease, disorder or condition in a subject, in particular an inflammatory disease, disorder or condition of the digestive tract such as inflammatory bowel disease (IBD) and/or colorectal cancer. The invention also relates to probiotic compositions and the use of the compositions for treating gastrointestinal disorders.

13 Claims, 18 Drawing Sheets

Specification includes a Sequence Listing.

(51) Int. Cl.

| | |
|---|---|
| ***C12P 7/52*** | (2006.01) |
| ***A61K 31/19*** | (2006.01) |
| ***A23K 10/18*** | (2016.01) |
| ***A61P 1/00*** | (2006.01) |
| ***A61P 29/00*** | (2006.01) |
| ***A61K 9/00*** | (2006.01) |
| ***A61K 9/50*** | (2006.01) |
| ***A61K 35/742*** | (2015.01) |
| *A61K 35/00* | (2006.01) |

(52) U.S. Cl.
CPC .............. *A61K 9/0056* (2013.01); *A61K 9/50* (2013.01); *A61K 35/742* (2013.01); *A61P 1/00* (2018.01); *A61P 29/00* (2018.01); *A23V 2002/00* (2013.01); *A61K 2035/115* (2013.01)

(58) Field of Classification Search
CPC ...... A61K 35/742; A61K 9/0056; A61K 9/28; A61K 9/50; A61P 1/00; A61P 1/04; A61P 1/06; A61P 29/00; A61P 31/04; A61P 35/00; A61P 43/00; C12N 15/52; C12P 7/42; C12P 7/52; C12P 7/54
See application file for complete search history.

(56) References Cited

FOREIGN PATENT DOCUMENTS

| | | | |
|---|---|---|---|
| WO | WO 2008/033352 | A2 | 3/2008 |
| WO | WO 2008/144423 | A2 | 11/2008 |
| WO | WO 2009/089144 | A1 | 7/2009 |
| WO | WO 2010/094789 | A1 | 8/2010 |
| WO | WO 2017/153734 | A1 | 9/2017 |
| WO | WO 2017/184788 | A1 | 10/2017 |

OTHER PUBLICATIONS

Ardizzone, S., et al., "Mongersen, an oral Smad7 antisense oligonucleotide, in patients with active Crohn's disease," *Therapeutic Advances in Gastroenterology* (2016), 9 (4): p. 527-32.

Atreya, I., et al., "NF-kappaB in inflammatory bowel disease," *Journal of Internal Medicine* (2008), 263 (6): p. 591-96.

Altschul, et al., "Basic local alignment search tool," *J. Mol. Biol.* (1990), 215(3): p. 403-10.

Berry, et al., "Detection, quantification, and characterisation of HIV/SIV," *Methods Mol. Biol.*(2011), 665, p. 133-60.

De Weirdt, et al., "Human faecal microbiota display variable patterns of glycerol metabolism," *FEMS Microbiol. Ecol.* (2010), 74 (3): p. 601-11.

Fantini, M. C., et al., "Cutting edge: TGF-beta induces a regulatory phenotype in CD4+CD25− T cells through Foxp3 induction and down-regulation of Smad7," *The Journal of Immunology* (2004), 172 (9): p. 5149-53.

Frank, D. C., et al., "Molecular-phylogenetic characterization of microbial community imbalances in human inflammatory bowel diseases," *Proc. Natl. Acad. Sci. USA.*, (2007), 104 (34): p. 13780-5.

Fu, SP., et al., "Anti-inflammatory effects of BHBA in both in vivo and in vitro Parkinson's disease models are mediated by GPR109A-dependent mechanisms," *J. Neuroinflammation.* (2015), 12 (9): p. 1-14.

Hamer, H. M., et al., "Review article: the role of butyrate on colonic function," *Ailment Pharmacol Ther.* (2008), 27 (2): p. 104-19.

Hannan, et al., "Generation of multipotent foregut stem cells from human pluripotent stem cells," *Stem Cell Reports* (2013), 1, p. 293-306.

Holscher, T., et al., "Production of the chiral compound (R)-3-hydroxybutyrate by a genetically engineered methylotrophic bacterium," *Apl. Environ. Microbiol.* (2010), 76 (16): p. 5585-91.

Molly, et al., "Development of a 5-step multi-chamber reactor as a simulation of the human intestinal microbial ecosystem," *Applied Microbiology and Biotechnology* (1993), 39 (2): p. 254-58.

Nakanishi, S. et al., "Rapid species identification and partial strain differentiation of Clostridium butyricum by PCR using 16S-23S rDNA intergenic spacer regions," *Microbiol. Immunol.* (2005), 49 (7): p. 613-21.

Neurath, M. F., "Cytokines in inflamatory bowl disease," *Nature Reviews Immunology* (2014), 14, p. 329-42.

Neurath, M. F., "Current and emergin therapeutic targets for IBD," *Nature Reviews Gastroenterology & Hepatology* (2017), 14, p. 269-78.

Popoff, et al., "Selective medium for isolation of Clostridium butyricum from human feces.," *J. Clin. Microbiol.* (1984), 20 (3): p. 417-20.

Teng, M. W. L., et al., "IL-12 and IL-23 cytokines: from discovery to targeted therapies for immune-mediated inflammatory diseases," *Nature Medicine* (2015) 21(7): p. 719-29.

Wang, T., et al., "Structural segregation of gut microbiota between colorectal cancer patients and healthy volunteers," *The ISME Journal* (2012), 2, p. 320-9.

Kovaleva, et al. "Methylobacterium and its role in health care-associated infection," *Journal of Clinical Microbiology* (2014), 52 (5): p. 1317-21.

Riviere, A. et al. "Bifidobacteria and Butyrate-Producing Colon Bacteria: Importance and Strategies for Their Stimulation in the Human Gut," *Frontiers in Microbiology* (2016), 7 (979): p. 1-21. doi: 10.3389/fmicb.2016.00979.

* cited by examiner atgactcaaagaatagcttatgtgactggaggaatgggtggaataggaactgcaatatgccaaaggttagctaaagatggatttagagtagttgctg
gatgtggtccaaactctccaagaagagaaagatggcttgaacagcaaaaagctttaggttttgactttgtagcaagtgaaggaaacgttgctgactg
ggattcaactaagacagcttttgataaagttaaagcagaagttggagaggtagatgtattaataaataatgctggaataactagagacgttgtttttaga
aaaatgacaagagcagactgggatgcagtaattgatactaatttaactagcttatttaatgtgactaagcaagtaatagacggtatggctgatagagga
tggggaagaatagtaaatatatcaagtgtaaacggtcagaaaggtcaatttggacagacaaattattcaacagcaaaagctggattacatggttttact
atggcattagcacaggaagttgcaacaaagggagttactgttaatactgtttctccaggatatattgcaacagatatggttaaagcaattagacaagac
gttttagacaaaattgtaggaacaatacctgttaaaagacttggagagcctgaggagattgcaagtatttgcgcttggctttcatctgatgaaagtggttt
ttctacaggtgcagattttagtttaaatggtggtcttcacatgggttagtaa

Figure 2

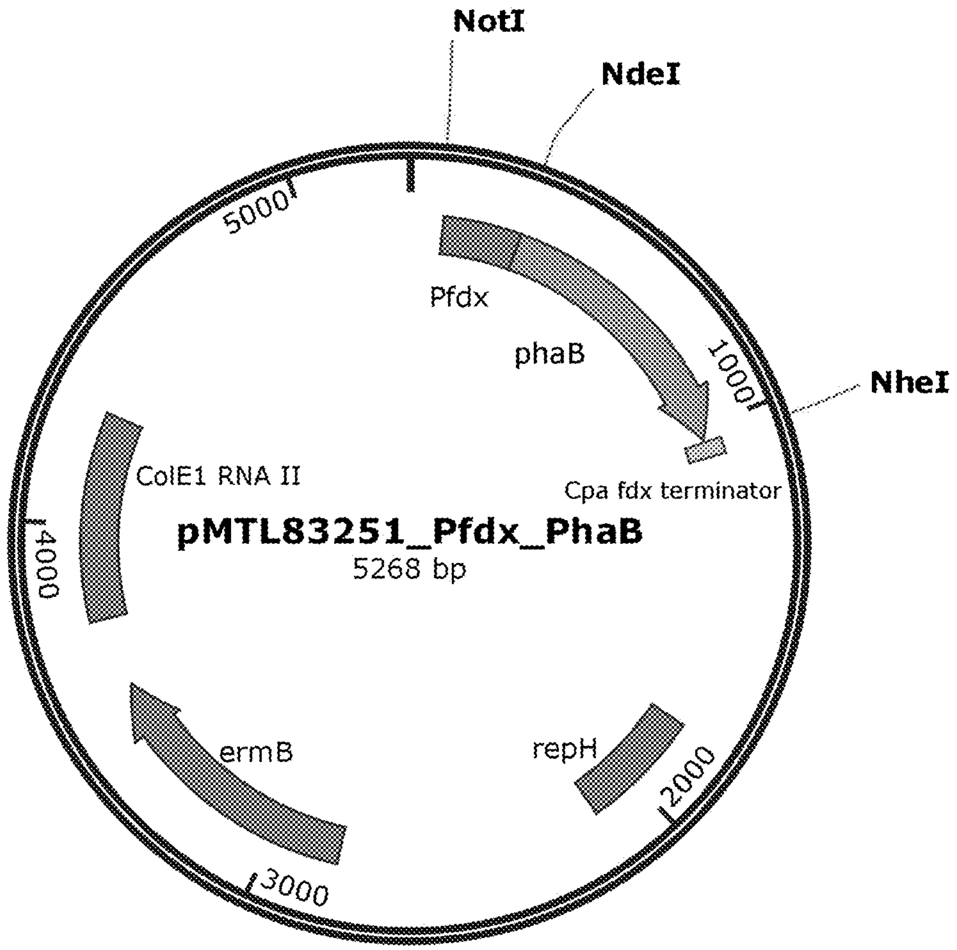

Figure 3

COMPOSITIONS AND USES THEREOF FOR TREATING INFLAMMATORY DISEASES AND PROBIOTIC COMPOSITIONS

CROSS-REFERENCE TO RELATED APPLICATIONS

This application is a National Stage Application, filed under 35 U.S.C. 371, of International Application No. PCT/GB2017/052832, filed on Sep. 21, 2017, which claims priority to Great Britain Patent Application No. 1616058.2, filed on Sep. 21, 2016 and Great Britain Patent Application No. 1706751.3, filed on Apr. 27, 2017, the contents of each of which are herein incorporated by reference in their entirety.

INCORPORATION BY REFERENCE OF SEQUENCE LISTING

The Sequence Listing associated with this application is provided in text format in lieu of a paper copy, and is hereby incorporated by reference into the specification. The name of the text file containing the Sequence Listing is CHBI-001N01US_Sequence_Listing.txt. The text file is 2.17 KB, was created on Mar. 20, 2019, and is being submitted electronically via EFS-Web.

FIELD

The invention relates to 3-hydroxybutyric acid (3-HB) or a salt thereof for use in a method of treating an inflammatory disease, disorder or condition in a subject, in particular an inflammatory disease, disorder or condition of the digestive tract such as inflammatory bowel disease (IBD) and/or colorectal cancer. The invention also relates to probiotic compositions comprising the compositions described herein and the use of the compositions for treating gastrointestinal disorders.

BACKGROUND

Inflammation is a complex reaction of the immune system that involves the accumulation and activation of leucocytes and plasma proteins at the site of infection, toxin exposure or cell injury. Although inflammation serves as a protective function in controlling infections and promoting tissue repair, it can also cause tissue damage and disease. IBDs, for example Crohn's disease and ulcerative colitis, are accompanied by aberrant intestinal inflammatory responses. Uncontrolled inflammation can also drive tumorigenesis in the intestine and patients with IBD have an increased risk of developing colorectal cancer.

It has been suggested that a specific network of cytokines and proteins are involved in the regulation of inflammation, in particular inflammation of mucosal tissue such as intestinal mucosa, which is implicated in the pathogenesis of diseases such as IBD. Drug therapies to date, including aminosalicylates and steroids, provide symptomatic improvement but fail to stop the underlying inflammatory process and do not change the disease course.

Biological agents such as antibodies have provided alternative treatment options for these chronic diseases by targeting inflammatory cytokines or proteins.

The pro-inflammatory cytokine TNF-α is an example of a cytokine that plays a key role in inflammation, and specifically in intestinal inflammation (Neurath, M. F. (2014) *Nature Reviews Immunology;* 14: 329-342). TNF-α activates fibroblasts, stimulates pro-inflammatory cytokine production and angiogenesis, induces death of epithelial cells, mediates T cell resistance against apoptosis and induces cachexia. Anti-TNF-α agents have been the focus of much work and a number of agents have been approved clinically for treating inflammatory diseases such as psoriasis, Crohn's disease and rheumatoid arthritis (Neurath, M. F. (2014) *Nature Reviews Immunology;* 14: 329-342). Examples include the monoclonal antibodies infliximab (Remicade®), adalimumab (Humira®), certolizumab pegol (Cimzia®), and golimumab (Simponi®).

IL-12 and IL-23 also play a role in inflammation and specifically have been associated with intestinal inflammation (Teng, M. W. L., et al. (2015) *Nature Medicine;* 21: 719-729). IL-12 and IL-23 are induced in the inflamed mucosa of patients with Crohn's disease. IL-12 induces type 1 T helper ($T_H1$) cells and Crohn's disease has been found to be associated with a $T_H1$ response. Type 17 T helper ($T_H17$) cell responses have been identified in Crohn's disease and ulcerative colitis and IL-23 is well-known as an activator of $T_H17$ cells. IL-12 and IL-23 share a subunit (p40) and the marketed drug ustekinumab targets this subunit and is approved for Crohn's disease. Risankizumab is specific for the p19 subunit unique to IL-23 and Phase 2 data suggest efficacy in Crohn's disease. (Neurath, M. F. (2017) *Nature Reviews Gastroenterology & Hepatology;* 14: 269-278). Other anti-IL-23 agents are in clinical development for treating inflammatory diseases such as psoriasis, psoriatic arthritis, ankylosing spondylitis and rheumatoid arthritis.

The pro-inflammatory cytokine IL-6 also plays a role in inflammation and specifically has been associated with intestinal inflammation (Neurath, M. F. (2014) *Nature Reviews Immunology;* 14: 329-342). IL-6 activates T cells and prevents apoptosis, induces macrophage activation, recruits immune cells, activates acute-phase proteins, induces proliferation of epithelial cells and favours tumour growth (Neurath, M. F. (2014) *Nature Reviews Immunology;* 14: 329-342). Anti-IL-6 drugs in development (e.g. tocilizumab) have shown early clinical efficacy for treating Crohn's disease. In IBD patients, IL-6 and its agonistic soluble receptor sIL-6R are induced and mediate T cell activation and their resistance of apoptosis. IL-6 blockage is effective in experimental colitis (Neurath, M. F. (2017) *Nature Reviews Gastroenterology & Hepatology;* 14: 269-278). Anti-IL-6 agents are also in clinical development for treating inflammatory diseases such as rheumatoid arthritis and have been approved for cancer therapy.

Blockade of IL-1β activity was shown to reduce tumorigenesis in mice by impairing macrophage-dependent IL-6 secretion. Deficiency of the IL-1β converting enzyme (ICE; also known as caspase 1)—an enzyme that cleaves IL-1β and IL-18 into active cytokines protected mice from dextran sulfate sodium (DSS)-induced colitis, which suggests that blockade of IL-1 family members may be relevant for the therapy of chronic intestinal inflammation (Neurath, M. F. (2014) *Nature Reviews Immunology;* 14: 329-342).

IL-10 suppresses pro-inflammatory cytokine production by antigen-presenting cells and T cells and induces STAT3 signaling in regulatory T cells. IL-10 has been implicated in inflammatory diseases, in particular intestinal inflammation such as colitis. For example, IL-10 deficiency is associated with IBD (Neurath, M. F. (2014) *Nature Reviews Immunology;* 14: 329-342).

TGF-β1 is produced by many immune and nonimmune cells in the gut of mice and humans and the two TGF-β1 receptors (type I and type II) are expressed on virtually all intestinal cells. TGF-β1 suppresses the activation and function of effector T cells and macrophages and contributes to the peripheral differentiation of both regulatory Foxp3-expressing T cells (Fantini, M. C., et al. (2004) *J Immunol;* 172: 5149-5153) and $T_H17$ cells. It also provides a chemotactic gradient for leukocytes and other cells participating in inflammatory responses and inhibits cells once they have become activated. TGF-β1 inhibits the production of extracellular matrix-degrading proteases by stromal cells and at the same time stimulates these cells to make collagen and promotes margination of epithelial cells. TGF-β1 is the major cytokine involved in the production of mucosal immunoglobulin A (IgA). Consistent with data generated in mouse models of inflammation, blockade of endogenous TGF-β1 activity in cultures of normal, intestinal mucosal cells or explants with a neutralizing antibody enhances induction of inflammatory molecules while stimulation of normal intestinal immune cells with recombinant TGF-β1 abrogates inflammatory signals. Mongersen is a drug in development to treat Crohn's disease. Mongersen restores TGF-β1 activity by knockdown of an inhibitor of TGF-β1 (Smad7) thus leading to suppression of inflammatory pathways and resolution of colitis in mice (Ardizzone, S., et al. (2016) *Ther Adv Gastroenterol;* 9(4): 527-532).

Cytokines activate tumour cell proliferation, expansion and survival through the activation of intracellular signaling molecules, such as STAT3 and NF-κB (Neurath, M. F. (2014) *Nature Reviews Immunology;* 14: 329-342). NF-κB is a protein complex that controls transcription of DNA, cytokine production and cell survival. The chronic mucosal inflammation in IBD is caused by hyperactivation of effector immune cells, which produce high levels of pro-inflammatory cytokines like TNF-α, IL-6 and interferon-γ, resulting in colonic tissue damage. The nuclear transcription factor NF-κB was identified as one of the key regulators in this immunological setting. Trinitrobenzene sulphonic acid (TNBS)-induced colitis can successfully be treated by local administration of p65 (subunit of NF-κB) antisense oligonucleotides and the NF-κB pathway is an attractive target for therapeutic interventions in IBD. As for all cytokines and proteins involved in IBD, NF-κB is also involved in normal cell physiology. Blockade of NF-κB activation in murine hepatocytes was associated with spontaneous development of hepatocellular carcinoma, so it would be desirable to restrict inhibition of NF-κB locally to immune cells within inflamed colonic mucosa (Atreya, I. et al. (2008) *Journal of Internal Medicine;* 263: 591-596).

Tissue remodeling and destruction in IBD is controlled by matrix metalloproteinases (MMPs). Expression of MMP9 was found to be increased in IBD, in particular ulcerative colitis patients. In vivo animal studies suggest an important role of MMP9 in impairing epithelial permeability and augmenting inflammation (Neurath, M. F. (2017) *Nature Reviews Gastroenterology & Hepatology;* 14: 269-278).

Biological agents targeting cytokines and proteins, for example monoclonal antibodies, are by their nature highly specific to their target. Antibody therapy is also often associated with secondary failure and withdrawal due to intolerance in the long term (Amiot, A. et al. (2015) *Ther Adv Gastroenterol;* 8(2): 66-82).

Miyarisan Pharmaceutical Co Ltd (Japan) produces a *Clostridium butyricum* (CBM 588 strain) probiotic for digestive health. This product uses a non-engineered *Clostridium* strain, which does not produce 3-HB. *C. butyricum* is found in the human gut microbiota and has a safe history of use as a probiotic for human and animal health.

There remains a need in the art for new therapeutics for treating inflammatory diseases, disorders or conditions, in particular inflammatory diseases, disorders or conditions in the intestinal tract including colorectal cancer. There remains a need in the art for therapeutics that suppress the inflammatory process underlying the disease, disorder or condition and/or are able to change the course of the disease, disorder or condition. New therapeutics are needed that are more efficacious; have fewer side effects; are orally acceptable; are easy to administer and exhibit improved compliance to treatment schedules; and/or are targeted for treating the disease, disorder or condition locally at the site of inflammation.

SUMMARY OF THE INVENTION

In a first aspect, the invention provides 3-hydroxybutyric acid (3-HB) or a salt thereof for use in a method of treating an inflammatory disease, disorder or condition in a subject.

In a second aspect, the invention provides a pharmaceutical composition comprising 3-HB or a salt thereof for use in a method of treating an inflammatory disease, disorder or condition in a subject.

In a third aspect, the invention provides a pharmaceutical composition for use in a method of treating an inflammatory disease, disorder or condition in a subject, wherein the composition comprises a 3-HB delivery means and the method comprises delivering the 3-HB delivery means to the lumen and/or mucosal surface of the gastrointestinal (GI) tract.

In a fourth aspect, the invention provides a method of treating an inflammatory disease, disorder or condition in a subject comprising administering to the subject: a) 3-hydroxybutyric acid (3-HB) or a salt thereof; b) a pharmaceutical composition comprising 3-HB or a salt thereof; and/or c) a pharmaceutical composition comprising a 3-HB delivery means.

In a fifth aspect, the invention provides a composition comprising, or consisting essentially of, genetically engineered anaerobic bacteria that produce (R)-3-HB, and an orally ingestible carrier.

In a sixth aspect, the invention provides a method of treating or preventing a gastrointestinal disease or disorder comprising administering genetically engineered anaerobic bacteria that produce (R)-3-hydroxybutyrate.

In a seventh aspect, the invention provides a method of treating or preventing a gastrointestinal dysbiosis comprising administering genetically engineered anaerobic bacteria that produce (R)-3-hydroxybutyrate.

In an eighth aspect, the invention provides a method of treating or preventing a *Clostridium difficile* infection comprising administering genetically engineered anaerobic bacteria that produce (R)-3-hydroxybutyrate.

In a ninth aspect, the invention provides a method for modulating gut flora in a subject comprising administering genetically engineered anaerobic bacteria that produce (R)-3-hydroxybutyrate.

BRIEF DESCRIPTION OF THE FIGURES

FIG. 2 shows the codon optimised DNA sequence for: the phaB gene from *Cupriavidus necator*.

FIG. 3 details the plasmid map for pfdx_phaB in pMTL83251 (*C. butyricum*)

DETAILED DESCRIPTION

Figure 1A:
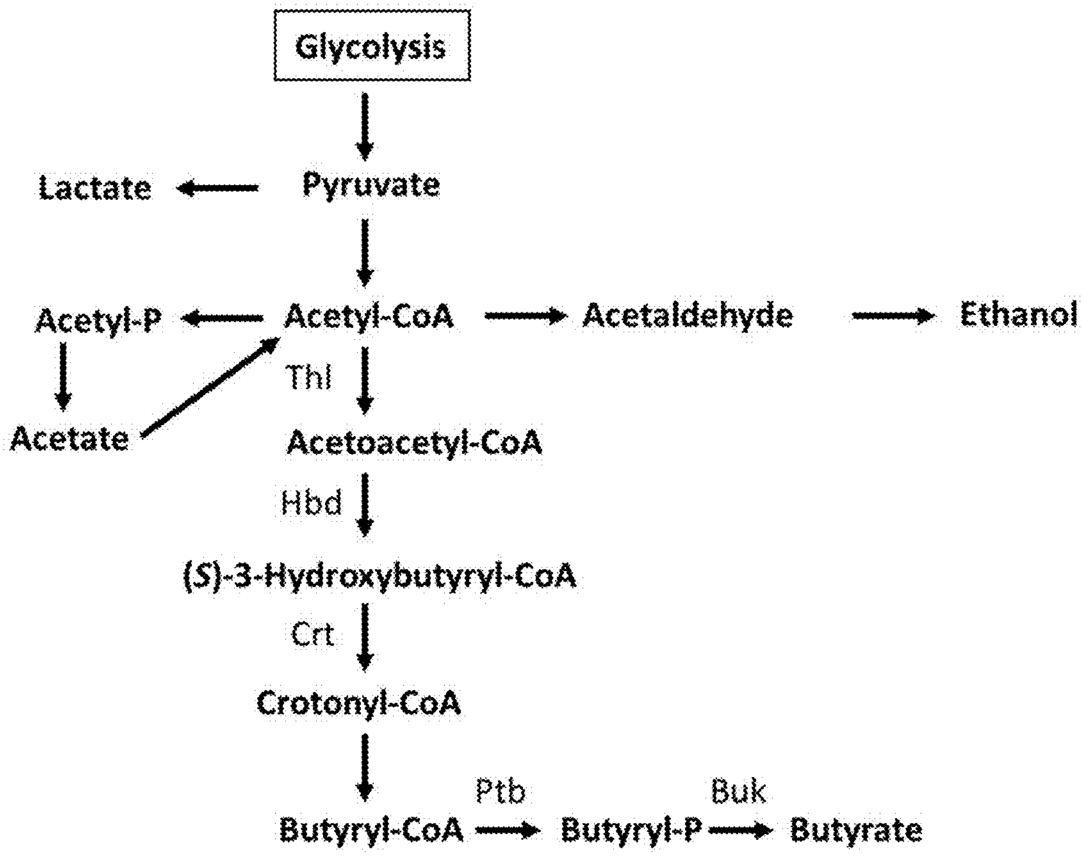
FIG. 1A shows the native acid production metabolic pathways in *Clostridium*.

The invention described herein is based upon the inventors' surprising discovery that 3-HB, and specifically the (R)-isomer (R)-3-hydroxybutyrate ((R)-3-HB), is a potent anti-inflammatory agent that acts on a number of different inflammatory cytokines and signalling molecules produced from intestinal cells. In particular, the inventors have shown that 3-HB downregulates certain pro-inflammatory cytokines and proteins (e.g. TNF-α, IL-23, IL-6, IL-1β, IL-12 and MMP9) and upregulates certain anti-inflammatory cytokines (e.g. IL-10, TGF-β1) in inflamed intestinal tissue. The cytokines and proteins involved have been implicated in a number of inflammatory diseases, disorders or conditions, in particular inflammation in the GI tract including IBDs (e.g. Crohn's disease, ulcerative colitis and colorectal cancer).

The invention addresses the above-mentioned needs in the art. In particular, the invention provides an improved therapy for treating an inflammatory disease, disorder or condition that has a broad effect on a number of different inflammatory cytokines and proteins.

The inventors have shown that 3-HB exhibits anti-inflammatory effects when delivered locally to inflamed tissue, specifically intestinal tissue. The invention thus provides an improved therapy for treating an inflammatory disease, disorder or condition that can be delivered locally to the site of inflammation.

The invention provides an improved therapy for treating an inflammatory disease, disorder or condition that suppresses the underlying inflammatory process and/or changes the disease course.

In some cases, the invention provides a preventative treatment, or therapy, for colorectal cancer.

In particular, the invention provides an improved therapy for an inflammatory disease, disorder or condition compared to biological agents such as antibodies that target individual cytokines. Specifically, 3-HB has a broader effect on a number of different inflammatory cytokines and proteins in inflamed tissue compared to such biological agents.

In certain aspects, the invention relates to pharmaceutical compositions that deliver 3-HB to the GI tract.

Gut microbiota have been implicated in promoting colonic health. One of the mechanisms by which this is thought to be achieved is through production of the short-chain fatty acids (SCFAs) acetate, propionate and butyrate by fermentation of dietary fibre. Butyrate has received most attention for its effects on colonic health, in particular as a key mediator of anti-inflammatory and anti-tumorigenic effects. Gut microbiome analysis has revealed a significant decrease in the number of butyrate-producing bacteria in colon of patients with ulcerative colitis and colon cancer (Frank, D. N., et al. (2007) *Proc Natl Acad Sci;* 104(34): 13780-13785; Wang, T., et al. (2012) *The ISME Journal;* 6: 320-329). It has been shown that colonic irrigation with butyrate can suppress inflammation during ulcerative colitis (Hamer, H. M., et al. (2008) *Aliment Pharmacol Ther;* 27: 104-119).

The inventors have also shown that 3-HB reduces the relative expression levels of several pro-inflammatory cytokines and proteins and increases the relative expression levels of anti-inflammatory cytokines to a greater extent than butyrate in inflamed tissue, specifically intestinal tissue.

Specifically, (R)-3HB has been shown to have a greater reducing effect on expression of 11-23 than Butyrate at low concentrations (10-100 μM).

(R)-3-HB, also known as D-β-hydroxybutyrate (β-OHB), is a ketone body naturally produced in the liver and circulated via the blood stream to extrahepatic tissues where it can act as a metabolic substrate during periods of carbohydrate restriction. (R)-3-HB also functions in various signalling pathways but is not normally found in the gut lumen of adults. Ingestion of 3-HB in the dissociated (acid) form is impractical. The acid may be formulated as a salt or ester product for ingestion but in these scenarios, 3-HB is rapidly absorbed in the small intestine and enters the blood stream where it is diluted and distributed systemically. Oral administration of salts of 3-HB is also unsuitable due to potentially dangerous high salt concentrations (e.g., sodium salts) in these formulations.

The invention provides pharmaceutical compositions that can be administered enterally, preferably orally. The invention thus provides an orally acceptable and well-tolerated pharmaceutical composition for delivering 3-HB. The pharmaceutical compositions exhibit improved patient compliance compared to adherence to a ketogenic diet, for example.

3-HB can be delivered to the intestines, preferably to the anaerobic sections of the intestines, preferably the large intestines and preferably the colon. The 3-HB can be delivered such that it is not absorbed in the small intestine. Preferably, the 3-HB is not delivered to the oesophagus, stomach or small intestines. The invention also provides pharmaceutical compositions that can be administered enterally, preferably rectally.

The 3-HB can therefore be delivered to the site of inflammation, specifically to the lumen of the GI tract, where it exhibits an effect locally. Adverse side effects are thus minimised or avoided. In particular, adverse side effects (e.g., salt overload) associated with the delivery and systemic uptake of therapeutically effective amounts of ketone bodies are minimised or avoided.

3-HB is a chiral compound having two isomers, (R)-3-HB and (S)-3-HB. 3-HB according to the invention can be an individual isomer, a racemic mixture of isomers or a non-racemic mixture of isomers. A racemic mixture of (R)-3-HB and (S)-3-HB can have about 50%/wt (R)-3-HB and about 50%/wt (S)-3-HB. Alternatively, at least about 50, 60, 70, 80 or 90%/wt of the 3-HB can be (R)-3-HB, the remainder being (S)-3-HB. Preferably, substantially all or 100%/wt of the 3-HB can be (R)-3-HB.

The molar ratio of (R)-3-HB to (S)-3-HB can be greater than 5:1, greater than 10:1, greater than 50:1, or greater than 100:1. In one embodiment the ratio of (R)-3-HB to (S)-3-HB is in the range of about 100-5:1, 100-50:1, 100-20:1, 50-5:1, 20-5:1, 15-5:1 or about 15-10:1.

3-HB is available commercially as a pure enantiomer in the (R) or (S)-form or as a racemic mixture of (R)-3-HB and (S)-3-HB. 3-HB can also be produced by methods known in the art. Preferably, 3-HB can be produced by fermentation of anaerobic bacteria genetically engineered to produce 3-HB. 3-HB can be isolated by methods known in the art. Preferably, 3-HB can be produced by fermentation of novel *Clostridium* strains described herein that produce chiral compounds. For example, 3-HB that can be 100%/wt (R)-3-HB can be produced by fermenting a *Clostridium* species, preferably *Clostridium butyricum*, comprising a heterologous gene capable of expressing (R)-3-hydroxybutyryl-CoA dehydrogenase. Increased titres can be achieved by the simultaneous introduction of heterologous genes capable of expressing butyrate kinase and phosphotransbutyrylase. The introduction of the heterologous gene capable of expressing (R)-3-hydroxybutyryl-CoA dehydrogenase results in the production of the (R) form of 3-hydroxybutyryl-CoA. Native reductase enzymes then convert (R)-3-hydroxybutyryl-CoA to (R)-3-HB. Alternatively, 3-HB that can be at least about 90%/wt (R)-3-HB with the remainder being (S)-3-HB can be produced by fermenting a *Clostridium* species, preferably, *Clostridium butyricum* comprising a heterologous gene capable of expressing (R)-3-hydroxybutyryl-CoA dehydrogenase. Increased 3-HB titres can be achieved via the introduction of a heterologous gene capable of expressing a propionyl-CoA transferase (PCT). The introduction of the heterologous (R)-3-hydroxybutyryl-CoA dehydrogenase and propionyl-CoA transferase gene results in the production of (R)-3-HB and (S)-3-HB at a ratio of about 10:1.

3-HB can be in the form of a pharmaceutically acceptable salt or solvate. "3-HB" as used herein refers to 3-HB or a salt thereof. A "pharmaceutically acceptable salt" as referred to herein, is any salt preparation that is appropriate for use in a pharmaceutical application. Pharmaceutically acceptable salts include amine salts, such as N,N'-dibenzylethylenediamine, chloroprocaine, choline, ammonia, diethanolamine and other hydroxyalkylamines, ethylenediamine, N-methylglucamine, procaine, N-benzylphenethylamine, 1-para-chloro-benzyl-2-pyrrolidin-1'-ylmethylbenzimidazole, diethylamine and other alkylamines, piperazine, tris(hydroxymethyl)aminomethane and the like; alkali metal salts, such as lithium, potassium, sodium and the like; alkali earth metal salts, such as barium, calcium, magnesium and the like; transition metal salts, such as zinc, aluminum and the like; other metal salts, such as sodium hydrogen phosphate, disodium phosphate and the like; mineral acids, such as hydrochlorides, sulfates and the like; and salts of organic acids, such as acetates, lactates, malates, tartrates, citrates, ascorbates, succinates, butyrates, valerates, fumarates and the like.

While it is possible for 3-HB to be administered alone, it is preferable for 3-HB to be present in a pharmaceutical composition. Consequently, the invention provides a pharmaceutical composition comprising 3-HB or a salt thereof for use in a method of treating an inflammatory disease, disorder or condition in a subject. Preferably, the pharmaceutical composition is formulated to deliver the 3-HB to the GI tract by releasing the 3-HB in the lumen or mucosal surface of the GI tract.

Alternatively, a pharmaceutical composition can deliver the 3-HB to the lumen or mucosal surface of the GI tract by other means. Consequently, the invention provides a pharmaceutical composition for use in a method of treating an inflammatory disease, disorder or condition in a subject, wherein the composition comprises a 3-HB delivery means and the method comprises delivering the 3-HB delivery means to the lumen or mucosal surface of the GI tract.

A "3-HB delivery means" can mean any chemical or biological means for delivering 3-HB or a salt thereof to the lumen of the GI tract. Suitable examples include a prodrug of 3-HB or a biological delivery system that delivers the 3-HB to the lumen of the GI tract. Such delivery means are discussed further below.

The present invention includes pharmaceutical compositions comprising at least one pharmaceutically acceptable carrier, and optionally other therapeutic and/or prophylactic ingredients.

The pharmaceutical compositions of the invention are administered such that a therapeutically effective amount of 3-HB is delivered and by any of the accepted modes of administration for agents that serve similar utilities.

Pharmaceutical compositions include those suitable for oral or rectal administration. Preferably, administration is oral using a convenient daily dosage regimen that can be adjusted according to the degree of affliction.

Pharmaceutical compositions of the invention can be prepared with one or more conventional adjuvants, carriers, or diluents and placed into dosage forms, such as unit dosages. The pharmaceutical compositions and dosage forms can be comprised of conventional ingredients in conventional proportions and the dosage forms can contain any suitable effective amount of the active agent (3-HB as described herein) commensurate with the intended daily dosage range to be employed.

Pharmaceutical compositions may take any of a number of different forms depending, in particular, on the manner in which it is to be used. Thus, for example, the agent or composition may be in the form of a powder, tablet, capsule, liquid, cream, gel, hydrogel, foam, micellar solution, liposome suspension or any other suitable form that may be administered to a person or animal in need of treatment. It will be appreciated that the carrier of the pharmaceutical composition according to the invention should be one which is well-tolerated by the subject to whom it is given.

A "pharmaceutically acceptable carrier" as referred to herein, is any known compound or combination of known compounds that are known to those skilled in the art to be useful in formulating pharmaceutical compositions.

The active agent may be used in a monotherapy (i.e. use of the active agent alone) for treating an inflammatory disease, disorder or condition in a subject. Alternatively, the active agent may be used as an adjunct to, or in combination with, one or more additional active agents including: 5-Aminosalicylates (5-ASAs), such as 5-ASA, mesalamine, sulfasalazine, olsalazine and balsalazide, specifically Asacol HD®, Delzicol®, Pentasa®, Lialda® and Apriso®; steroids, in particular corticosteroids such as hydrocortisone, methylprednisolone, prednisone, prednisolone and budesonide; immunomodulators including immunosuppressive drugs such as azathioprine, 6-mercaptopurine, methotrexate, ciclosporin-A and tacrolimus; biologic agents including anti-TNF agents such as infliximab, adalimumab, golimumab and certolizumab pegol, T-cell trafficking agents such as integrin blockers natalizumab and vedolizumab, antibiotics and probiotics including nonpathogenic microorganisms such as commensal *Escherichia coli, Lactobacillus species, Saccharomyces* or the parasite *Trichuris suis*; chemotherapy agents for colorectal cancer such as capecitabine (Xeloda®), fluorouracil (5-FU, Adrucil®), irinotecan (Camptosar®), oxaliplatin (Eloxatin®) and trifluridine/tipiracil (TAS-102, Lonsurf®); targeted therapies for colorectal cancer including anti-angiogenesis therapies such as bevacizumab (Avastin®), regorafenib (Stivarga®), ziv-aflibercept (Zaltrap®) and ramucirumab (Cyramza®), and Epidermal growth factor receptor (EGFR) inhibitors such as cetuximab (Erbitux®) and panitumumab (Vectibix®); short chain fatty acids such as butyrate, for example butyric acid. 3-HB can be used in combination with any one or more of the above, for example in combination with azathioprine and infliximab. Preferably, 3-HB can be used in combination with butyrate.

In one preferred embodiment, the pharmaceutically acceptable carrier may be a solid, and the composition may be in the form of a powder or tablet. A solid pharmaceutically acceptable carrier may include one or more substances which may also act as flavouring agents, buffers, lubricants, stabilizers, solubilizers, suspending agents, wetting agents, emulsifiers, dyes, fillers, glidants, compression aids, inert binders, sweeteners, preservatives, dyes, coatings, or tablet-disintegrating agents. The carrier may also be an encapsulating material. In powders, the carrier is a finely divided solid that is in admixture with the finely divided active agents according to the invention. In tablets, the active agent may be mixed with a carrier having the necessary compression properties in suitable proportions and compacted in the shape and size desired. The powders and tablets preferably contain up to 99% of the active agents. Suitable solid carriers include, for example, calcium phosphate, magnesium stearate, talc, sugars, lactose, dextrin, starch, gelatine, cellulose, polyvinylpyrrolidine, low melting waxes and ion exchange resins. In another embodiment, the pharmaceutically acceptable carrier may be a gel and the composition may be in the form of a cream or the like.

The carrier may include one or more excipients or diluents. Examples of such excipients are gelatin, gum arabicum, lactose, microcrystalline cellulose, starch, sodium starch glycolate, calcium hydrogen phosphate, magnesium stearate, talcum, colloidal silicon dioxide and the like.

However, in another preferred embodiment, the pharmaceutically acceptable carrier may be a liquid, and the pharmaceutical composition is in the form of a solution. Liquid carriers are used in preparing solutions, suspensions, emulsions, syrups, elixirs and pressurized compositions. The active agent according to the invention may be dissolved or suspended in a pharmaceutically acceptable liquid carrier such as water, an organic solvent, a mixture of both or pharmaceutically acceptable oils or fats. The liquid carrier can contain other suitable pharmaceutical additives such as solubilizers, emulsifiers, buffers, preservatives, sweeteners, flavouring agents, suspending agents, thickening agents, colours, viscosity regulators, stabilizers or osmo-regulators. Suitable examples of liquid carriers for oral administration include water (partially containing additives as above, e.g. cellulose derivatives, preferably sodium carboxymethyl cellulose solution), alcohols (including monohydric alcohols and polyhydric alcohols, e.g. glycols) and their derivatives, and oils (e.g. fractionated coconut oil and *arachis* oil).

Pharmaceutical compositions of the invention may be administered orally in the form of a sterile solution or suspension containing other solutes or suspending agents (for example, enough saline or glucose to make the solution isotonic), bile salts, acacia, gelatine, sorbitan monoleate, polysorbate 80 (oleate esters of sorbitol and its anhydrides copolymerized with ethylene oxide) and the like. The agents used according to the invention can also be administered orally either in liquid or solid composition form. Compositions suitable for oral administration include solid forms, such as pills, capsules, granules, tablets, and powders, and liquid forms, such as solutions, syrups, elixirs, and suspensions, including capsules containing liquid forms, all of which are known to those skilled in the art.

Pharmaceutical compositions of the invention can also be formulated for rectal administration including suppositories and enema formulations. In the case of suppositories, a low melting wax, such as a mixture of fatty acid glycerides or cocoa butter is first melted and the active component is dispersed homogeneously, for example, by stirring. The molten homogeneous mixture is then poured into convenient sized molds, allowed to cool, and to solidify. Enema formulations can be semi-solid including gels or ointments or in liquid form including suspensions, aqueous solutions or foams, which are known to those skilled in the art.

Other suitable pharmaceutical carriers and their formulations are described in Remington: The Science and Practice of Pharmacy 22nd Edition, The pharmaceutical Press, London, Philadelphia, 2013.

Pharmaceutical compositions of the invention can be formulated as modified-release dosage forms. By "modified release" is meant that the dosage forms are formulations where the rate and/or site of release of the active agent(s) are different from that of the immediate release dosage form administered by the same route. This modification is achieved by special formulation design and/or manufacturing methods. Modified release dosage forms include orally administered modified release dosage forms. Prolonged release (or extended release) dosage forms are modified release dosage forms that show a sustained release over a prolonged period of time. In delayed release dosage forms, release of the active substance is delayed for a certain period of time after administration or application of the dosage (the delay is also known as the lag time). The subsequent release can be similar to that of an immediate release dosage form. Multiphasic release dosage forms include biphasic release and pulsatile release. In biphasic release dosage forms, the first phase of drug release is determined by a fast release dose fraction providing a therapeutic drug level shortly after administration; and the second extended release phase provides the dose fraction required to maintain an effective therapeutic level for a prolonged period. Pulsatile drug release is intended to deliver a burst of drug release at specific time intervals. Multiple-unit: A multiple unit dosage form contains a plurality of units e.g. pellets or beads each containing release controlling excipients, e.g. in a gelatine capsule or compressed in a tablet. Single-unit: The single-unit dosage forms consist of only one unit, e.g. osmotic tablet.

Excipients and formulations for modified-release are well-known in the art and specific technologies are commercially available.

Suitably, pharmaceutical compositions of the invention are formulated to deliver 3-HB to the GI tract, preferably by oral administration. The human GI tract consists of digestive structures stretching from the mouth to the anus, including the oesophagus, stomach, and intestines. The GI tract does not include the accessory glandular organs such as the liver, biliary tract or pancreas. The intestines includes the small intestine and large intestine. The small intestine includes the duodenum, jejunum and ileum. The large intestine includes the cecum, colon, rectum and anus. The upper GI tract includes the buccal cavity, pharynx, oesophagus, stomach, and duodenum. The lower GI tract includes the small intestine below the duodenum and the large intestine. Preferably, the pharmaceutical compositions of the invention deliver the 3-HB to the lumen or mucosal surface of the GI tract, more preferably the lumen or mucosal surface of the large intestine, and more preferably the lumen or mucosal surface of the colon. Preferably, the pharmaceutical compositions of the invention deliver 3-HB to anaerobic sections of the GI tract, preferably the colon and/or terminal small intestine (ileum).

Various strategies have been proposed for targeting orally administered drugs to the colon, including: covalent linkage of a drug with a carrier, including those that enhance stability as well as increasing hydrophilicity; coating with pH-sensitive polymers; formulation of timed released systems; exploitation of carriers that are degraded specifically by colonic bacteria; bioadhesive systems; and osmotic controlled drug delivery systems. Various prodrugs have been developed that are aimed to deliver 5-aminosalicylic acid (5-ASA) for localized treatment of IBD. Microbially degradable polymers, especially azo-crosslinked polymers, have been investigated for use as coatings for drugs targeted to the colon. Certain plant polysaccharides such as amylose, inulin, pectin, and guar gum remain unaffected in the presence of gastrointestinal enzymes and have been explored as coatings for drugs for the formulation of colon-targeted drug delivery systems. Additionally, combinations of plant polysaccharides with crustacean extract, including chitosan or derivatives thereof, are proving of interest for the development of colonic delivery systems.

Examples of excipients for modified-release formulations include hydrogels that are able to swell rapidly in water and retain large volumes of water in their swollen structures. Different hydrogels can afford different drug release patterns and the use of hydrogels to facilitate colonic delivery has been investigated. For example, hydrogels and xerogels have been prepared using a high-viscosity acrylic resin gel, Eudispert hv, which has excellent staying properties in the lower part of the rectum over a long period. Eudragit® polymers (Evonik Industries) offer different forms of coating including gastro resistance, pH-controlled drug release, colon delivery, protection of and protection from actives.

Pharmaceutical compositions may be prepared according to any of the techniques known in the art, for example by mixing 3-HB, one or more pharmaceutically acceptable carrier, excipient and/or diluent and one or more modified-release excipient. Pharmaceutical compositions may be prepared by coating a core comprising 3-HB and one or more pharmaceutically acceptable carrier, excipient and/or diluent and optionally one or more modified-release excipient with a modified-release layer or coating using techniques in the art. For example, coatings may be formed by compression using any of the known press coaters. Alternatively, the pharmaceutical compositions may be prepared by granulation and agglomeration techniques, or built up using spray drying techniques, followed by drying.

Coating thickness can be controlled precisely by employing any of the aforementioned techniques. The skilled person can select the coating thickness as a means to obtain a desired lag time, and/or the desired rate at which drug substance is released after the lag time.

pH-dependent systems exploit the generally accepted view that pH of the human GI tract increases progressively from the stomach (where pH can be between about 1 and 2, which increases to pH 4 during digestion), through the small intestine (where pH can be between about 6 and 7) at the site of digestion, increasing in the distal ileum. Coating tablets, capsules or pellets with pH-sensitive polymers provides delayed release and protects the active drug from gastric fluid.

The pharmaceutical compositions of the invention can be formulated to deliver 3-HB to the GI tract at a particular pH. Commercially available excipients include Eudragit® polymers that can be used to deliver 3-HB at specific locations in the GI tract. For example, the pH in the duodenum can be above about 5.5. Eudragit® L 100-55 (Powder), Eudragit® L 30 D-55 (Aqueous dispersion), and/or Acryl-EZE® (Powder) can be used, for example as a ready-to-use enteric coating based on Eudragit® L 100-55. The pH in the jejunum can be from about 6 to about 7 and Eudragit® L 100 (Powder) and/or Eudragit® L 12,5 (Organic solution) can be used. Delivery to the colon can be achieved at a pH above about 7.0 and Eudragit® S 100 (Powder), Eudragit® S 12,5 (Organic solution), and/or Eudragit® FS 30 D (Aqueous dispersion) can be used. PlasACRYL™ T20 glidant and plasticizer premix, specifically designed for Eudragit® FS 30 D formulations can also be used.

The pharmaceutical compositions can be formulated to deliver the 3-HB at a pH of about 5.5 or more, such as about 5.6, 5.7, 5.8 or 5.9 or more; preferably 6 or more, such as about 6.1, 6.2, 6.3, 6.4, 6.5, 6.6, 6.7, 6.8 or 6.9 or more; preferably 7 or more, such as about 7.1, 7.2, 7.3, 7.4, 7.5, 7.6, 7.8, 7.9 or 8. Preferably, the pharmaceutical compositions can be formulated to deliver the 3-HB at a pH of between about 5.5 and 7, between about 6 and 7.5, or between 7 and 8. In one embodiment, the pharmaceutical composition releases the 3-HB or 3-HB delivery means at the appropriate pH, thus delivering the 3-HB to the lumen of the GI tract, preferably to the terminal ileum and/or colon.

A pharmaceutical composition taken on an empty stomach is likely to arrive in the ascending colon about 5 hours after dosing, with the actual arrival dependent largely on the rate of gastric emptying. Drug delivery within the colon is greatly influenced by the rate of transit through this region. In healthy men, capsules and tablets pass through the colon in 20-30 hours on average. Solutions and particles usually spread extensively within the proximal colon and often disperse throughout the entire large intestine.

The pharmaceutical compositions of the invention can be formulated for time-controlled delivery to the GI tract, i.e. to deliver the 3-HB after a certain time (lag time) following administration.

Commercially available excipients for time-controlled delivery include Eudragit® RL PO (Powder), Eudragit® RL 100 (Granules), Eudragit® RL 30 D (Aqueous dispersion), and Eudragit® RL 12,5 (Organic solution). These excipients are insoluble, high permeability, pH-independent swelling excipients that can provide customized release profiles by combining with Eudragit® RS at different ratios. Eudragit® RS PO (Powder), Eudragit® RS 100 (Granules), Eudragit® RS 30 D (Aqueous dispersion), and Eudragit® RS 12,5 (Organic solution) are insoluble, low permeability, pH-independent swelling excipients that can provide customized release profiles by combining with Eudragit® RL at different ratios. Eudragit® NE 30 D (Aqueous dispersion), Eudragit® NE 40 D (Aqueous dispersion), and Eudragit® NM 30 D (Aqueous dispersion) are insoluble, low permeability, pH-independent swelling excipients that can be matrix formers.

Preferably, the pharmaceutical compositions can be formulated to deliver the 3-HB to the GI tract about 4 hours after administration. Preferably, the pharmaceutical compositions can be formulated to deliver the 3-HB between about 4 and 48 hours after administration, preferably between about 5 and 24 hours after administration, such as about 5, 10, 15, 20 or 24 hours after administration; preferably between about 5 and 10, 5 and 15, 5 and 20, or between about 10 and 24, 15 and 24 or 20 and 24 hours after administration. Preferably the pharmaceutical compositions are for administration between meals or with food, preferably with food. In one embodiment, the pharmaceutical composition releases 3-HB after the lag time. Alternatively, the pharmaceutical composition releases the 3-HB delivery means after the lag time.

Release of 3-HB or the 3-HB delivery means from the pharmaceutical compositions at the appropriate pH or after the lag time can be either immediate release or modified release. Immediate release and modified release formulations are known to those skilled in the art.

Release of the 3-HB or 3-HB delivery means from the pharmaceutical compositions can be measured by methods known in the pharmaceutical industry. Drug dissolution testing is routinely used to provide critical in vitro drug release information for both quality control purposes (to assess batch-to-batch consistency of solid oral dosage forms such as tablets) and drug development (to predict in vivo drug release profiles). Dissolution testing can be conducted in dissolution apparatus including USP Dissolution Apparatus 1—Basket (37° C.); USP Dissolution Apparatus 2—Paddle (37° C.); USP Dissolution Apparatus 3—Reciprocating Cylinder (37° C.); USP Dissolution Apparatus 4—Flow-Through Cell (37° C.).

Preferably, substantially no 3-HB is released from the pharmaceutical compositions until the appropriate pH is reached and/or until the lag time has expired. Preferably, substantially no 3-HB delivery means is released from the pharmaceutical compositions until the appropriate pH is reached and/or until the lag time has expired. Preferably not more than 10%/wt of the 3-HB or 3-HB delivery means is released from the pharmaceutical compositions, preferably not more than 9, 8, 7, 6, 5, 4, 3, 2 or 1%/wt of the 3-HB or 3-HB delivery means is released from the pharmaceutical compositions until the appropriate pH is reached and/or until the lag time has expired.

In a specific embodiment, pharmaceutical compositions can be formulated using Multi Matrix MMX® technology (Cosmo Pharmaceuticals Inc.), preferably as tablets. Tablets manufactured according to the MMX® technology are coated with pH-resistant acrylic copolymers which delay the release until the tablet reaches the indicated intestinal location where the programmed dissolution begins, thus protecting the active agents from adverse pH conditions and enzymatic presence in the upper GI tract. Modified release over the length of the colon not only simplifies the application for the patients but allows for the topical application of the active pharmaceutical ingredients to the surface that is affected by inflammation. For example, pharmaceutical compositions can be formulated as Zacol NMX® (Cosmo Pharmaceuticals Inc.) tablets can include calcium 3-HB, Maltodextrin, Inulin, Sorbitol, Hypromellose, Microcrystalline Cellulose, Modified Corn starch, Citric Acid, Colloidal Silica Hydrate, Talc, Shellac, Magnesium Stearate, stearic Acid, Lecithin, Titanium Dioxide, Hydroxypropyl, Triethyl Citrate; Aroma: vanillin.

In another embodiment, pharmaceutical compositions can be formulated as a BioCare® capsule containing 3-HB buffered with calcium and magnesium (3-hydroxybutyric acid, calcium hydroxide, magnesium hydroxide and medium chain triglicerides), the capsule shell comprising hydroxypropyl methylcellulose, and comprising anti-caking agents silicon dioxide and magnesium stearate. Capsules are approximately 2.3 cm long.

Pharmaceutical compositions may be over-coated with a pharmaceutically acceptable film-coating, for aesthetic purposes (e.g. including a colourant), for stability purposes (e.g., coated with a moisture barrier), for taste-masking purposes, or for the purpose of protecting the 3-HB, prodrug, delivery system and/or excipients from aggressive media. Preferably, the pharmaceutical compositions can be over-coated with a gastro-protective or enteric coating, for example represented by a mixture of acrylic and/or methacrylic acid copolymers type A and/or type B (as, for example, Eudragit S100 and/or Eudragit L100). Preferably, the mixture of acrylic and/or methacrylic acid copolymers type A and/or type B is in a range ratio from 1:5 to 5:1. The gastro-protective coating also optionally comprises plasticizers, dyes, at least one water-solvent, at least one organic solvent or a mixture thereof.

By "prodrug" is meant a derivative of a drug molecule that requires a transformation within the body to release the active drug. A colonic drug delivery strategy involves the use of a prodrug which is metabolized by enzymes found only in the colon.

Biological Delivery System

In one embodiment, a pharmaceutical composition that delivers 3-HB to the GI tract contains a biological delivery system capable of producing 3-HB.

By "biological delivery system" is meant a biological agent, such as a microbiological agent, preferably a bacterial agent that can be administered orally and is capable of producing 3-HB. Preferably, the biological delivery system can be genetically engineered anaerobic bacteria capable of producing 3-HB. The bacteria may produce 3-HB as either the sole fermentation product or in combination with short chain fatty acids (SCFAs), such as acetate and/or butyrate.

Compositions of the invention can comprise genetically engineered anaerobic bacteria that produce 3-HB and an orally ingestible carrier. The composition can deliver 3-HB to a subject. Once orally ingested the bacteria will subsequently grow in the subject and produce and secrete 3-HB into the anaerobic parts of the gastrointestinal tract. The bacterium may secrete 3-HB as it transits through the gut or when it becomes attached to the epithelial/mucosal cell wall lining.

The bacteria can be anaerobic bacteria. Anaerobic bacteria are bacteria that can survive in an oxygen limited (hypoxic) environment or a completely oxygen depleted (anoxic) environment. These include obligate anaerobes, which are bacteria that are harmed by the presence of oxygen and can only grow in anaerobic (no oxygen) environments; aerotolerant bacteria, which can survive in an aerobic environment (with oxygen) but cannot use molecular oxygen as a terminal electron acceptor in their respiratory pathways; and facultative anaerobes, which can survive in both aerobic and anaerobic environments and can use molecular oxygen or another molecule as a terminal electron acceptor in their respiratory pathways, depending on availability of their preferred electron acceptor. Preferably, the bacteria are obligate anaerobes.

In one embodiment the bacteria are Clostridia. The introduction of a non-native gene capable of expressing (R)-3-HB dehydrogenase ((R)-3-HBD) results in a Clostridial strain that can produce (R)-3-HB. The engineered Clostridia produce (R)-3-hydroxybutyryl-CoA. Native PTB and BUK enzymes, if present, can convert (R)-3-hydroxybutyryl-CoA into (R)-3-HB. (R)-3-HB is secreted into the gut.

Clostridia that naturally produce butyrate as the main fermentation product have now been adapted to produce (R)-3-HB either instead of, or in combination with butyrate. The Clostridia may also produce other useful fermentation products such as acetate, propionate, vitamins and bacteriocins.

Bacteria that are part of the natural gut microbiota are preferred, i.e. those bacteria that are naturally found in the gut. Bacteria that naturally produce butyrate are also preferred. Clostridia are a preferred class of bacteria for including in the compositions. Clostridia can include but are not limited to Clostridiaceae, Christensenellaceae, Eubacteriaceae, Lachnospiraceae, Peptostreptococcaceae, Ruminococcacea. Preferably the bacteria present are from cluster I, IV and/or XIVa of Clostridia. Preferably the bacteria are Clostridia frequently detected in the lower gastrointestinal tract. For example, species detected in the lower gastrointestinal tract include:

Bacteria from the genus *Clostridium* (cluster 1), the preferred species for including in the composition include, but are not limited to, *C. acetobutylicum, C. arbusti, C. aurantibutyricum, C. beijerinckii, C. cellulovorans, C. cellulolyticum, C. thermocellum, C. thermobutyricum, C. pasteurianum, C. kluyveri, C. novyi, C. saccharobutylicum*, C. the rmosuccino genes, *C. thermopalmarium, C. saccharolyticum, C. saccharoperbutylacetonicum, C. tyrobutyricum, C. tetanomorphum, C. magnum, C. ljungdahlii, C. autoethanogenum, C. butyricum, C. puniceum, C. diolis*, C. 5 *homopropionicum* and/or *C. roseum;*

Bacteria from the genera Christensenellaceae, Eubacteriaceae, and Lachnospiraceae (cluster XIVa), the preferred species for including in the composition include, but are not limited to, *Roseburia intestinalis, Roseburia bromii, Eubacterium rectale, Eubacterium hallii, Anaerostipes* spp., *Butyrivibrio* spp. and/or *Coprococcus* spp; and Bacteria from the genus Ruminococcacea (cluster IV), the preferred species for including in the composition include, but are not limited to, *Faecalibacterium prausnitzii.*

Preferably the species in the composition is *C. butyricum.*

Preferably the Clostridia are butyrate producers. Well-known clostridial butyrate producers include *Anaerostipes* spp., *Butyrivibrio* spp., *Coprococcus* spp., *Roseburia* spp., *Eubacterium* rectale- and *Eubacterium hallii*-related species.

Preferably the *Clostridium* species in the composition are capable of sporulation, preferably *C. butyricum*. In a preferred embodiment, the strains are DSM10702 and ATCC19398.

The engineered bacteria can comprise a non-native gene capable of expressing (R)-3-HBD. Genes capable of expressing (R)-3-HBD (EC1.1.1.36) are selected from but are not restricted to genes from organisms including *Ralstonia eutropha*, (*Cupriavidus necator*), *Bacillus* sp, *Klebsellia* sp, *Pseudomonas* sp, for example phbB and phaB.

Suitable genes include UniProt Accession Nos. P14697 (PHBB_CUPNH), P50203 (PHAB_ACISR), A0A060V147 (A0A060V147_KLESP), C1D6J5 (C1D6J5_LARHH), F8GXX8 (F8GXX8_CUPNN), F8GP10 (F8GP10_CUPNN), GOETI7 (GOETI7_CUPNN), A9LLG6 (A9LLG6_9BACI), A0A0E0VPS5 (A0A0E0VPS5_STAA5), D5DZ99 (D5DZ99_BACMQ), and V6A8L4 (V6A8L4_PSEAI)

In one embodiment the (R)-3-HBD gene is phaB. The sequence of the phaB gene can be codon optimised for the specific *Clostridium* species used. The sequence of phaB may comprise the sequence as shown in FIG. 2 (SEQ ID NO:1).

The nucleic acid encoding the non-native (R)-3-HBD may comprise a sequence which has at least 60%, 70%, 80%, 90%, 95% or 99% sequence identity with the phaB sequence of FIG. 2 (SEQ ID NO:1).

A number of methods are available to determine identity between two sequences. A preferred computer program to determine identity between sequences includes, but is not limited to BLAST (Atschul et al, Journal of Molecular Biology, 215, 403-410, 1990). Preferably the default parameters of the computer programs are used.

In Clostridia, native enzymes can catalyse 3-hydroxybutyrate reductase reactions. Therefore, in one embodiment the *Clostridium* species comprise genes that encode enzymes able to convert (R)-3-hydroxybutyryl-CoA to (R)-3-HB.

Native enzymes, such as, PTB and BUK, convert (R)-3-hydroxybutyryl-CoA into (R)-3-HB via (R)-3-hydroxybutyrate-phosphate. Therefore, the genetically engineered bacteria can have native genes encoding for PTB and BUK and a non-native gene encoding (R)-3-HBD.

The *Clostridium* species may also comprise further non-native genes such as those encoding for PTB, BUK, PCT and/or BUT.

The *Clostridium* species can comprise one or more non-native genes encoding reductive enzymes able to convert (R)-3-hydroxybutyryl-CoA to (R)-3-HB, such as ptb and buk. These genes may come from organisms including but not limited to *Bacillus* species, *E. coli*, or from other species of Clostridia.

Additionally, the *Clostridium* species may comprise one or more native or non-native genes encoding enzymes to produce SCFA's, such as PCT or BUT. For example, a PCT from *Clostridium propionicum* can be engineered into a strain to catalyse the CoA transfer reaction between (R/S)-3-hydroxybutyrate-CoA and acetate.

The term "non-native gene" refers to a gene that is not in its natural environment, and includes a gene from one species of a microorganism that is introduced into another species of the same genus.

The non-native genes may be codon optimised for Clostridia and/or placed under the control of promoters that enable controllable expression of the gene in Clostridia. The expression levels of the enzymes can be optimised by controlling gene expression with inducible promoters and/or promoters with different strength. In one embodiment the non-native genes are placed under the control of a native Clostridia promoter, for example a ferredoxin or thiolase promoter. Other suitable promoters would be known to the person skilled in the art.

The non-native genes can be introduced in *Clostridium* strains by standard plasmid transformation techniques known in the art for producing recombinant microorganisms i.e. conjugation or electroporation. By way of example only, plasmid transformation is achieved by conjugation.

Non-native genes, including (R)-3-HBD, may be integrated into the chromosome of Clostridia using gene integration technology known to persons skilled in the art.

Clostridia are anaerobic bacteria with a fermentative metabolism that naturally convert carbohydrates into a variety of reduced fermentation products. The bacteria have unique metabolic pathways and biochemistry for producing three and four carbon (C3/C4) chemicals.

Figure 1B:
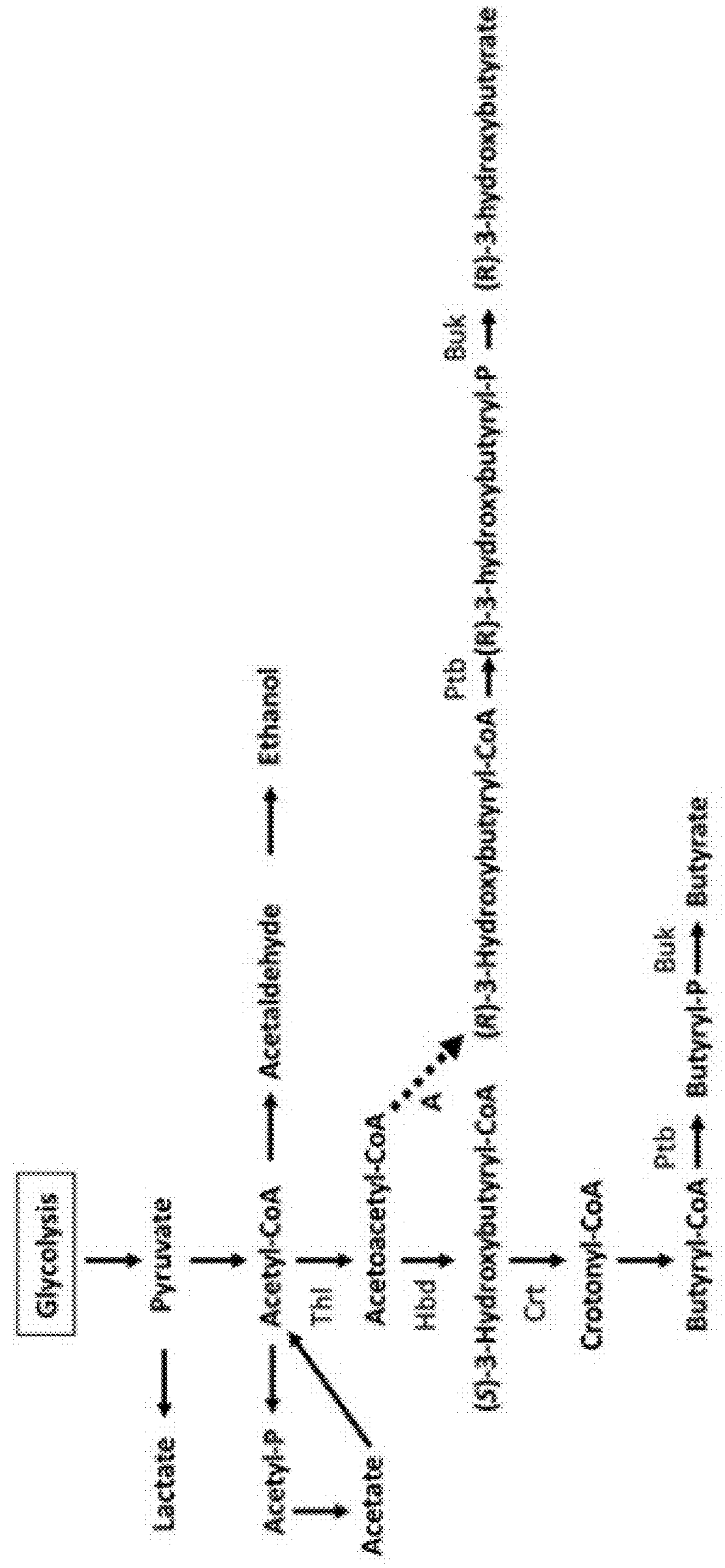
FIG. 1B shows the acid production metabolic pathways in *Clostridium* after the introduction of a non-native (R)-3-hydroxybutyryl-CoA dehydrogenase.

The metabolic pathway of a genetically engineered *Clostridium* strain is detailed in FIG. 1B. The genetically engineered *Clostridium* sp. carries a heterologous (R)-3-HBD (Enzyme A in FIG. 1B) that converts acetoacetyl-CoA into (R)-3-hydroxybutyryl-CoA. The (R)-specific 3-hydroxybutyryl-CoA dehydrogenase competes with the native HBD enzyme for the substrate (acetoacetyl-CoA). The native crotonase (Crt) enzyme has no or only low activity towards the (R)-form of 3-hydroxybutyryl-CoA, allowing (R)-3-hydroxybutyryl-CoA to be converted to (R)-3-HB via native enzymes, such as PTB and BUK or BUT. Enzymes PTB and BUK are specific for the R-form and convert (R)-3-hydroxybutyryl-CoA into (R)-3-HB via (R)-3-hydroxybutyryl-phosphate.

The pathway used will depend on the *Clostridium* species. In some species, typically those found in the Clostridiaceae family (cluster I), which includes the *Clostridium* genus (including *C. butyricum*) the final step requires two enzymes, PTB and BUK. In other species, typically those found in the Lachnospiraceae family (cluster XIVa) and Ruminococcaceae family (cluster IV) the final step requires one enzyme, BUT. Some Clostridia carry enzymes of both systems allowing them to convert (R)-3-hydroxybutyryl-CoA to (R)-3-HB.

If PTB, BUK and/or BUT are not present in the native probiotic strain, then heterologous genes encoding these enzymes can be expressed in the engineered strain.

An alternative route to produce (R)-3-HB in genetically engineered anaerobic bacteria is by the introduction of further non-native genes encoding, for example a thioesterase, i.e. TesB from *E. coli*. These enzymes can convert (S)- and (R)-3-hydroxybutyryl-CoA into (S)- and (R)-3-HB, respectively.

The *Clostridium* probiotic can be prepared by fermentation carried out under suitable conditions for growth of the bacteria. After fermentation, the bacteria can be purified using centrifugation and prepared to preserve activity. The bacteria in the composition are provided as viable organisms. The composition can comprise bacterial spores and/or vegetative cells. The bacteria can be dried to preserve the activity of the bacteria. Suitable drying methods include freeze drying, spray-drying, heat drying, and combinations thereof. The obtained powder can then be mixed with one or more pharmaceutically acceptable excipients as described herein.

The spores and/or vegetative bacteria may be formulated with the usual excipients and components for oral administration, as described herein. In particular, fatty and/or aqueous components, humectants, thickeners, preservatives, texturing agents, flavour enhancers and/or coating agents, antioxidants, preservatives and/or dyes that are customary in the pharmaceutical and food supplement industry. Suitable pharmaceutically acceptable carriers include microcrystalline cellulose, cellobiose, mannitol, glucose, sucrose, lactose, polyvinylpyrrolidone, magnesium silicate, magnesium stearate and starch, or a combination thereof. The bacteria can then be formed into a suitable orally ingestible form, as described herein. Suitable orally ingestible forms of probiotic bacteria can be prepared by methods well known in the pharmaceutical industry.

In one embodiment, the anaerobic bacteria that produce 3-HB can be present in the pharmaceutical composition in a wide range of concentrations provided the bacteria are present in an amount sufficient to provide the desired therapeutic effect. Preferably the bacteria are present in the pharmaceutical composition in an amount equivalent to between $1\times10^5$ to $1\times10^{10}$ colony forming units/g (CFU/g) of dry composition, more preferably the bacteria are present in an amount equivalent to between $1\times10^8$ to $1\times10^{10}$ CFU/g of dry composition. When the composition is in the form of a tablet the bacteria may be present in an amount of $2\times10^5$ to $6\times10^7$ CFU per tablet, preferably from about $3\times10^5$ to $5\times10^7$ CFU per tablet. Preferably, the bacteria grow and metabolise in the colon and deliver between about 1 μm and 10 mM 3-HB to the gut lumen, preferably between about 100 μm and 5 mM, preferably about 1 mM.

By "delivery of 3-HB" is meant that the 3-HB is made available at a particular site in the subject such that the 3-HB exhibits a therapeutic effect to treat the inflammatory disease, disorder or condition. The 3-HB can be delivered to a particular site of inflammation in the subject such that the 3-HB is available to have a therapeutic effect locally. Preferably, the pharmaceutical compositions of the invention deliver the 3-HB to the site of the inflammatory disease, disorder or condition and have a therapeutic effect locally. For example, 3-HB can be delivered rectally directly to the site of inflammation; the 3-HB can be released from an oral dosage form, such as a capsule or tablet described herein, at the site of inflammation; or the 3-HB can be released from a 3-HB delivery system, such as a prodrug or biological delivery system that produces the 3-HB at the site of inflammation.

The therapeutically effective amount of 3-HB that should be administered depends on the 3-HB utilized (e.g. the ratio of (R)- to (S)-isomers), the subject being treated, the severity and type of the affliction, and the manner and route of administration.

Considering the amount of 3-HB that is delivered, a therapeutically effective amount may be from about 0.1 mg per kilogram (kg) body weight to about 500 mg per kg body weight, for example about 1 mg to about 250 mg per kg body weight, for example about 10 mg to about 180 mg per kg body weight, for example about 20 mg to about 150 mg per kg body weight, for example about 60 mg to about 125 mg per kg body weight. For example, a therapeutically effective amount may be from about 10 mg to about 40 g, for example from about 80 mg to about 20 g, for example from about 100 mg to about 15 g, for example from about 1 g to about 12 g, for example from about 5 g to about 10 g.

For oral administration, a therapeutically effective amount may be from about 10 mg to about 20 g, for example from about 50 mg to about 20 g, for example from about 100 mg to about 20 g, for example from about 100 mg to about 10 g, for example from about 500 mg to about 10 g, for example from 500 mg to 5 g, for example from 500 mg to 2 g, for example from 1 g to 15 g, for example from 1 g to 10 g, for example from 1 g to 8 g, for example from 1 g to 2 g, for example from 1 g to 4 g, for example from 2 g to 4 g, for example from 2 g to 6 g, for example from 4 g to 8 g, for example from 4 g to 6 g, for example from 5 g to 10 g, for example from 6 g to 10 g, for example from 6 g to 8 g, for example from 8 g to 12 g, for example from 8 g to 10 g, for example from 10 g to 14 g, for example from 10 g to 12 g, for example from 10 g to 20 g. In a preferred embodiment, a therapeutically effective amount may be from about 10 mg to about 50 g, for example 10 mg to about 30 g, for example from about 50 mg to about 30 g, for example from about 100 mg to about 30 g, for example from about 100 mg to about 15 g or for example from about 500 mg to about 15 g. In another preferred embodiment, a therapeutically effective amount may be from about from 1 g to 50 g, for example from 5 g to 50 g, for example from 10 g to 40 g, for example 1 g to 30 g for example from 5 g to 30 g, for example from 3 g to 25 g, for example from 1 g to 20 g, for example from 5 g to 20 g, for example from 1 g to 10 g, for example from 20 g to 30 g, for example from 30 g to 40 g, or for example from 5 g to 15 g.

Each dose of a therapeutically effective amount may be several unit doses. A single solid unit dose may contain, for example, from about 50 mg to about 3 g, for example from about 100 mg to about 2 g, for example from about 250 mg to about 2 g, for example from about 500 mg to about 2 g, for example from about 250 mg to about 1 g, for example from about 500 mg to about 1 g, for example 100 mg to 500 mg, for example 100 mg to 1 g, for example 100 mg to 2 g, for example 250 mg to 2 g, for example 250 mg to 1 g, for example 500 mg to 2 g, for example 500 mg to 1 g, for example 1 g to 3 g, for example 1 g to 2 g. Specific unit doses that may be mentioned are about 1.5 g, 1.6 g, 1.7 g, 1.8 g, 1.9 g and 2 g, preferably about 1.8 g; or about 300 mg.

The dose amounts discussed above may be given, for example, once, twice, three times or four times a day or once or twice a week; preferably three times a day. For example, for oral administration, a total daily dose of from 30 mg to about 120 g may be given, for example from about 240 mg to about 60 g, for example from about 300 mg to about 45 g, for example from about 3 g to about 36 g or for example from about 15 g to about 30 g. In one preferred embodiment, the total daily dose for oral administration is, for example from about 1 g to about 50 g, for example from about 1 g to about 30 g, for example from about 5 g to about 30 g, for example from about 5 g to about 25 g, for example from about 5 g to about 15 g, preferably from about 5 g to about 10 g. Preferably, about 1.8 g is administered three times a day.

A dose can be administered as part of a meal or snack or liquid, wherein the subject is provided with a dry dose for mixing with or combining with the meal, snack or liquid (for example water or fruit juice).

In accordance with the invention, 3-HB can be administered in combination with one or more additional therapeutic agents. Administration includes administration of a formulation that includes the 3-HB and one or more additional therapeutic agents, or the essentially simultaneous, sequential or separate administration of separate formulations of the 3-HB and one or more additional therapeutic agents. In one embodiment, the 3-HB delivery means also delivers one or more additional therapeutic agents to the lumen of the GI tract, preferably wherein the additional therapeutic agent is butyrate.

The invention also encompasses methods of treating an inflammatory disease, disorder or condition in a subject.

A method of treating comprises administering 3-HB to a subject for the purposes of ameliorating a disease, disorder or condition (i.e., slowing or arresting or reducing the development of the disease, disorder or condition or at least one of the clinical symptoms thereof); alleviating or ameliorating at least one physical parameter including those which may not be discernible by the patient; modulating the disease, disorder or condition, either physically (e.g., stabilization of a discernible symptom), physiologically (e.g., stabilization of a physical parameter), or both; or preventing or delaying the onset or development or progression of the disease or disorder or a clinical symptom thereof.

A subject is in need of a treatment if the subject would benefit biologically, medically or in quality of life from such treatment. Treatment will typically be carried out by a physician who will administer a therapeutically effective amount of the 3-HB. Suitably the subject is a human.

A therapeutically effective amount of 3-HB refers to an amount that will be effective for the treatment described above, for example slowing, arresting, reducing or preventing the disease, disorder or condition or symptom thereof. Typically, a subject in need thereof is a subject presenting symptoms of the disease, disorder or condition. Alternatively, a subject may be susceptible to the disease, disorder or condition or has been tested positive for the disease, disorder or condition but has not yet shown symptoms.

Preferably, the therapeutically effective amount of 3-HB administered provides a concentration of 3-HB in the lumen of the GI tract, preferably in the colon, of between about 1 μM and about 10 mM, preferably between about 100 μM and about 5 mM, preferably about 1 mM.

The inflammatory disease, disorder or condition can be characterised by elevated pro-inflammatory cytokines or proteins and/or insufficient levels of anti-inflammatory cytokines or proteins; specifically those implicated in inflammatory diseases, disorders or conditions, in particular inflammatory diseases, disorders or conditions in the GI tract including IBDs such as Crohn's disease and ulcerative colitis, and colorectal cancer. Preferably, the inflammatory disease, disorder or condition is characterised by elevated levels of one or more of, preferably 2, 3, 4, 5, 6 or more or all of TNF-α, IL-23, IL-6, IL-1β, IL-12, MMP9 and NF-κB; preferably IL-23. Preferably, the inflammatory disease, disorder or condition is characterised by insufficient levels of IL-10 and/or TGF-β1 to achieve and maintain an appropriate immune response. Preferably, the inflammatory disease, disorder or condition is characterised by elevated levels of 2, 3, 4, 5, or more or all of TNF-α, IL-23, IL-6, IL-1β, IL-12 and MMP9 and by insufficient levels of IL-10 and/or TGF-β1 to achieve and maintain an appropriate immune response; preferably by elevated levels of TNF-α, IL-23, IL-6, IL-1β, IL-12 and MMP9 and by insufficient levels of IL-10 and TGF-β1, optionally further characterised by elevated levels of NF-κB.

The inflammatory disease, disorder or condition can be further characterised by elevated levels and/or insufficient levels of one or more of IL-8, IL-18, IL-18 binding protein, IL-16, Caspase-1, IL-1α, IL-17A and RANTES (CCL5), IL-22 and IL-27.

The inflammatory disease, disorder or condition can be an IBD such as Crohn's disease, ulcerative colitis, pouchitis, collagenous colitis and lymphocytic colitis, colorectal cancer, rheumatoid arthritis, multiple sclerosis, psoriasis, psoriatic arthritis, gout, ankylosing spondylitis or COPD.

Preferably, the inflammatory disease, disorder or condition is an inflammatory disease, disorder or condition of the GI tract, preferably of the large intestine, more preferably of the colon. Preferably, the inflammatory disease, disorder or condition is an IBD, preferably Crohn's disease or ulcerative colitis, or colorectal cancer.

The invention also relates to compositions comprising the biological delivery system, such as the genetically engineered anaerobic bacteria capable of producing (R)-3-HB, as described herein, and their use as probiotics in the treatment of gastrointestinal diseases and disorders, and for animal health.

The bacteria may be formulated with the usual excipients and components for such oral compositions, i.e. in particular fatty and/or aqueous components, humectants, thickeners, preservatives, texturing agents, flavour enhancers and/or coating agents, antioxidants, preservatives and/or dyes that are customary in the pharmaceutical and food supplement industry. Suitable pharmaceutically acceptable carriers include microcrystalline cellulose, mannitol, glucose, polyvinylpyrrolidone, and starch, or a combination thereof. The bacteria can then be formed into a suitable orally ingestible form. Suitable orally ingestible forms of probiotic bacteria can be prepared by methods well known in the pharmaceutical industry. The composition to be administered orally may be formulated for example in the form of coated tablets, gel capsules, gels, emulsions, tablets, capsules, hydrogels, food bars, compact or loose powders, liquid suspensions or solutions, confectionery products, or food carriers. Preferably the composition is in a dry form. The preferred oral form for the composition is a solid form such as a capsule, tablet or powder.

The compositions may be formulated via the usual processes for producing oral formulations in particular coated tablets, gel capsules, gels, emulsions, tablets, capsules, hydrogels and powders.

The orally ingestible carrier can also be a food product such as a beverage, a drink, a food supplement, or a nutraceutical.

The genetically engineered anaerobic bacteria that produce (R)-3-HB can also be incorporated as part of a food product, i.e. in yoghurt, milk or soy milk, or as a food supplement. Such food products and food supplements can be prepared by methods well known in the food and supplement industry.

The compositions can be incorporated into animal feed products as a feed additive.

The composition can also be used for preventing or treating dysbiosis. Gastrointestinal dysbiosis can be caused by the use of broad spectrum antibiotics. The compositions may be used for treating and preventing dysbiosis from the administration of antibiotics.

During dysbiosis, the subject is susceptible to opportunistic pathogenic microbes including *C. difficile*. The composition can be used to treat or to prevent bacterial infections. In one embodiment of the invention the composition can be used for the treatment or prevention of *C. difficile* infection.

Compositions comprising genetically engineered anaerobic bacteria that produce (R)-3-HB can also be used in modulating gut flora in a subject. The compositions comprising or consisting essentially of, genetically engineered anaerobic bacteria that produce (R)-3-HB are administered to a healthy subject, i.e. for a non-therapeutic use. The compositions can be administered orally to the subject.

The growth and degree of colonisation in the gut of the genetically engineered bacteria can be controlled by species and strain choice and/or by providing specific food that the bacteria thrive on as a prebiotic, either within the same dose that contains the probiotic or as a separately ingested composition.

The composition may also further comprise a prebiotic to enhance the growth of the administered probiotic. The prebiotic may be administered sequentially, simultaneously or separately with a composition comprising genetically engineered anaerobic bacteria that produce (R)-3-HB. The prebiotic and genetically engineered bacteria can be formulated together into the same composition for simultaneous administration. Alternatively, the bacteria and prebiotic can be formulated separately for simultaneous or sequential administration.

Prebiotics are substances that promote the growth of probiotics in the intestines. They are food substances that are fermented in the intestine by the bacteria. The addition of a prebiotic provides a medium that can promote the growth of the probiotic strains in the intestines. One or more monosaccharides, oligosaccharides, polysaccharides, or other prebiotics that enhances the growth of the bacteria may be used.

Preferably, the prebiotic may be selected from the group comprising of oligosaccharides, optionally containing fructose, galactose, mannose; dietary fibres, in particular soluble fibres, soy fibres; inulin; or combinations thereof. Preferred prebiotics are fructo-oligosaccharides (FOS), galacto-oligosaccharides (GOS), isomalto-oligosaccharides, xylo-oligosaccharides, oligosaccharides of soy, glycosylsucrose (GS), lactosucrose (LS), lactulose (LA), palatinose-oligosaccharides (PAO), malto-oligosaccharides, pectins, hydrolysates thereof or combinations thereof.

(R)-3-HB secreted from the bacteria may act locally within the lumen and/or within the mucosal layer of the gut, for example to modulate gut flora by acting as an enhancer and or suppressor of microbial growth.

All of the features described herein (including any accompanying claims, abstract and drawings), and/or all of the steps of any method so disclosed, may be combined with any of the above aspects in any combination, except combinations where at least some of such features and/or steps are mutually exclusive. Specifically, any of the active agents and compositions described herein can be used in any of the described methods of treatment. Any and all such combinations are explicitly envisaged as forming part of the invention.

EXAMPLES

The invention will now be explained in further detail with reference to the following Examples.

Example 1—Production of (R)-3-HB in *C. butyricum* Expressing phaB

1) Gene Synthesis

The gene *Cupriavidus necator* phaB was codon optimised for Clostridia. FIG. 2 shows one example of the codon optimised sequence which was synthesized by Gene Art® (Thermo Fisher Scientific).

2) Plasmid Assembly phaB was cloned into plasmid pMTL83251 under control of the *C. sporogenes* Pfdx promoter using standard cloning techniques yielding plasmid pMTL83251_pfdx_phaB (see FIG. 3)

3) Strain Development

Plasmid pMTL83251_pfdx_phaB was conjugated into *Clostridium butyricum* ATCC19398/DSM10702 using *E. coli* CA434 as conjugation donor. A strain specific conjugation protocol was applied. Briefly, overnight cultures of *E. coli* CA434 carrying plasmid pMTL83251_pfdx_phaB and *C. butyricum* were used to inoculate 9 ml LB and RC broth respectively. Cultures were grown until $OD_{600}$ of 0.5-0.7 was reached. 1 ml of *E. coli* culture was spun down and the pellet mixed with 200 μl heat-shocked (50° C. 10 min) *C. butyricum* culture. The cell mix was spotted on a non-selective RCM plate and incubated overnight. The incubated mix was re-suspended into 500 μl fresh RCM and plated on selective media containing 10 μg/ml erythromycin. Presence of the plasmid within the obtained transconjugants was confirmed by PCR using plasmid specific primers.

4) Fermentation Data for *C. butyricum*

Growth Method

RC broth containing per 1 L: yeast extract 13 g, Peptone 10 g, soluble starch 1 g, sodium chloride 5. g, sodium acetate 3 g, cysteine hydrochloride 0.5 g, carbohydrate 2%, was used. Calcium carbonate 10 g/L was added to liquid culture for pH regulation. Solid media contained 15 g/L agar.

Transformants were grown overnight in seed cultures (RC broth) at 37° C. 100 ml RC broth containing 2% glucose was inoculated to a starting OD of 0.05-0.1. Strains were grown anaerobically at 37° C. in the presence of required antibiotic. Samples for metabolic analysis were taken at regular intervals.

Analysis and Results

Figure 4A:
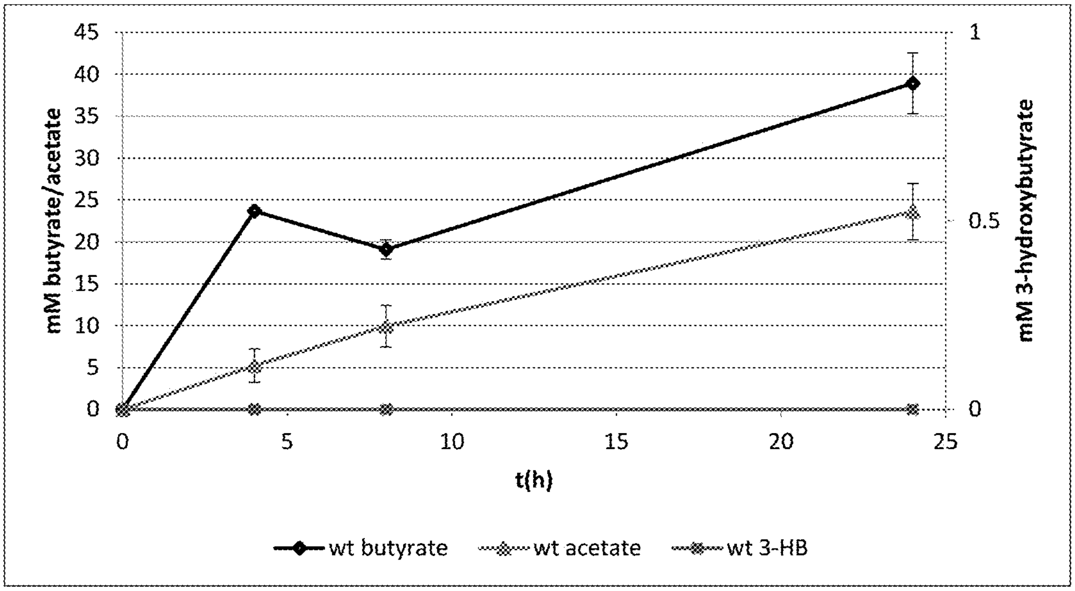
FIG. 4A shows the production of (R)-3-HB, butyrate and acetate produced by wildtype *C. butyricum* (wt).
Figure 4B:
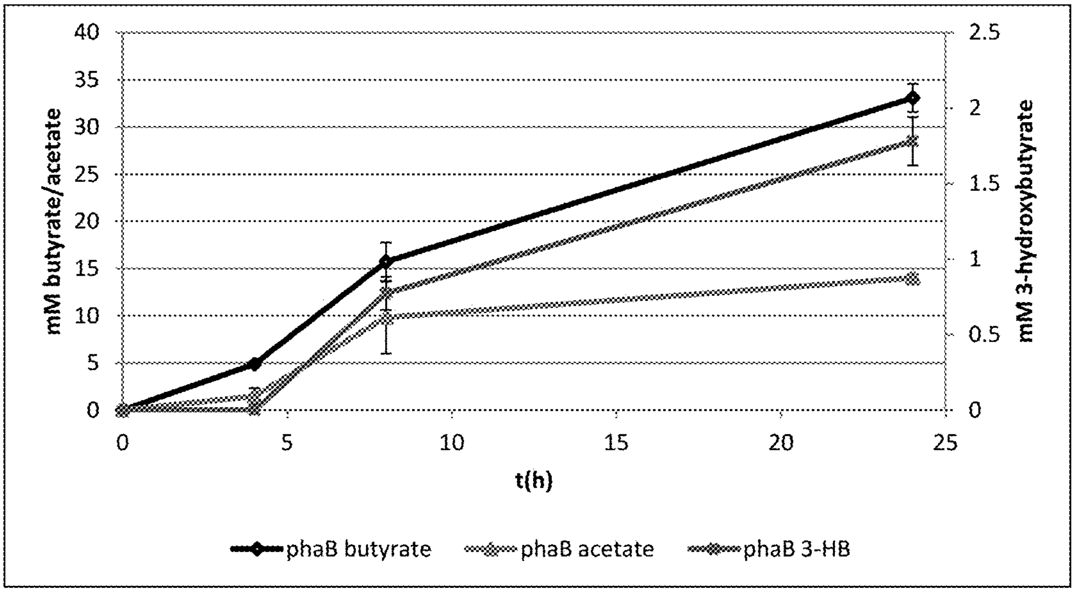
FIG. 4B shows the production of (R)-3-HB, butyrate and acetate produced by genetically engineered *C. butyricum* (CHN-1-phaB).

Culture supernatant of the engineered *C. butyricum* (CHN-1) was analysed for (R)-3-HB and (S)-3-HB using the 3-HB assay kit (Sigma Aldrich). The strain expressing phaB produced only (R)-3-HB. Culture supernatants of CHN-1 and a native *C. butyricum* were also analysed for production of SCFAs and (R)-3-HB using HPLC-RI. The phaB expression strain of *C. butyricum* (CHN-1) produced about 187 mg/L after 24 h growth as shown in FIG. 4B. The wildtype *C. butyricum* strain only produced butyrate and acetate as shown in FIG. 4A.

Example 2—Formulations for Colonic Delivery

Zacol NMX® is a dietary supplement (nutraceutical) based on the MMX® technology and directed to the colon. It is a product based on the application of MMX® technology to a combination of calcium salt of butyric acid and inulin. NMX® is a nutraceutical version of MMX® technology. Tablets contain calcium 3-HB (0.307 g), Maltodextrin, Inulin (0.250 g), Sorbitol, Hypromellose, Microcrystalline Cellulose, Modified Corn starch, Citric Acid, Colloidal Silica Hydrate, Talc, Shellac, Magnesium Stearate, stearic Acid, Lecithin, Titanium Dioxide, Hydroxypropyl, Triethyl Citrate; Aroma: vanillin.

BioCare format. Capsules contain 1815 mg 3-HB, 243 mg calcium hydroxide, 123 mg magnesium hydroxide, medium chain triglycerides, capsule shell (hydroxypropyl methylcellulose), anti-caking agents (silicon dioxide & magnesium stearate). One capsule is taken three times a day with food, or as professionally directed.

Example 3—Bacterial Delivery

Spore Formation of *C. butyricum*

Figure 5A:
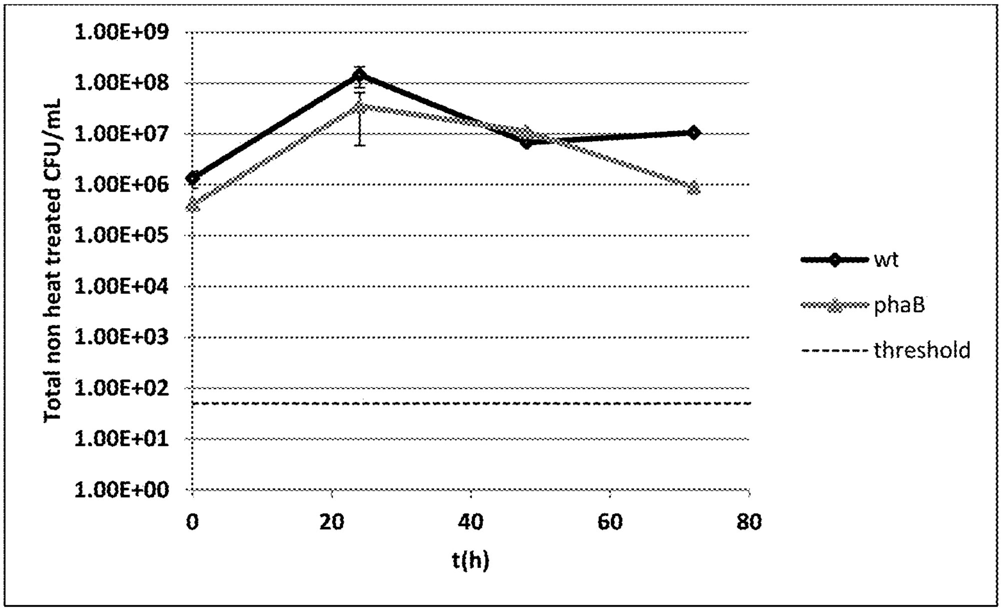
FIG. 5 shows the total CFU (A) and spores (heat-resistant CFU) (B) produced by wildtype *C. butyricum* and genetically engineered *C. butyricum* (CHN-1-phaB) measured as CFU/mL over time.
Figure 5B:
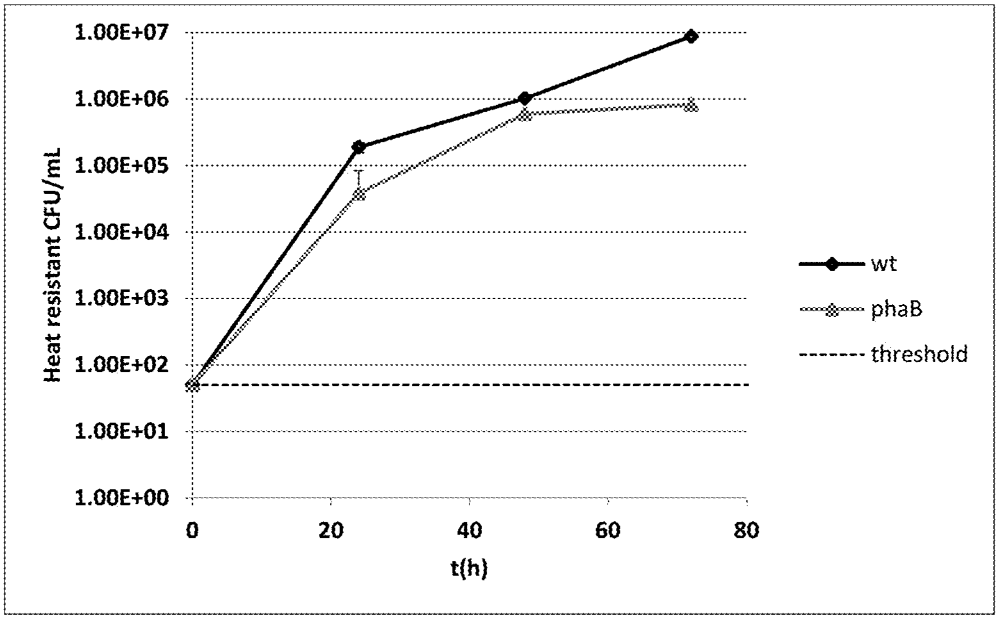
Figure 6:
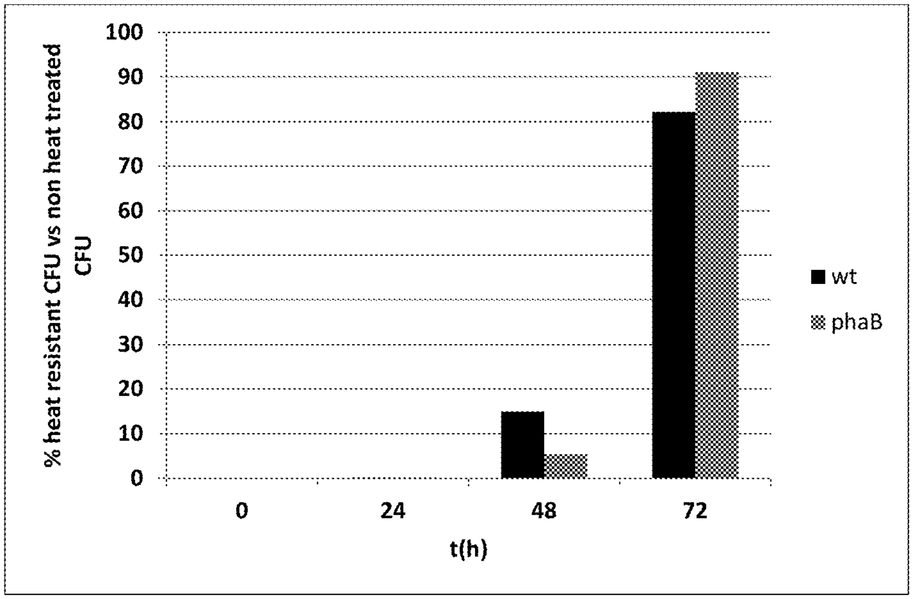
FIG. 6 shows the percentage of spores to vegetative cells produced by wildtype *C. butyricum* and genetically engineered *C. butyricum* (CHN-1-phaB) over time.

The same culture medium and inoculation techniques as for fermentation were used. Samples were taken at the start of the experiment and in regular intervals for 72 h to determine the ratio of vegetative cells to spores. For enumeration of spores, samples were heat treated at 65° C. for 30 min to kill any vegetative cells. Simultaneously, samples taken for enumeration of total CFU count (vegetative cells+spores), were placed on the bench to prevent further growth in the medium. Heat treated and non-heat treated samples were then serially diluted and plated in 20 μL discreet spots in triplicate on non-selective medium for wildtype and on selective medium for engineered strains. After overnight incubation at 37° C. anaerobically, CFU/mL were determined. FIGS. 5A-B show the development of spores over 72 hours. FIG. 6 shows the percentage of spores in total CFU in the culture over 72 hours.

Tablet formulations includes corn starch, lactose, hydrated magnesium silicate, microcrystalline cellulose, magnesium stearate and sucrose.

Example 4—Evaluation of CHN-1 in a Simulated Colon Environment

Spores of engineered *C. butyricum* (CHN-1) were produced using pH controlled laboratory scale bioreactors. Strains were handled in nitrogen and carbon dioxide flushed anaerobic workstations at 37° C. before inoculation into bioreactors.

CHN-1 was grown on Reinforced Clostridial agar (Sigma-Aldrich, UK) plates from spore stocks. A single colony was used to inoculate modified Reinforced Clostridial (RC) broth (per litre: Yeast 13 g, Peptone 10 g, Starch 1 g, NaCl 5 g, $CH_3COONa$ 3 g, Cysteine hydrochloride 0.5 g, $CaCO_3$ 10 g, Glucose 20 g), which was then serially diluted $10^{0}$-$10^{-8}$ in modified RC broth. After 8-12 hours, a 1:10 dilution was prepared in fresh modified RC from highest diluted o/n culture grown (usually $10^{-6}$) into a day culture. The day culture was typically grown 1½-2 hours before it was transferred into serum bottles. Serum bottles were capped with a rubber stopper to maintain anaerobiosis. Bacterial culture from the serum bottles was used to inoculate the bioreactor 1:10. Bioreactors contained modified RC, were pH controlled at 6.5 using 3M sterile KOH as required, with 125 rpm agitation and 6 L/h $N_2$ flushing. Bioreactors were maintained at 37° C. throughout. Cell mass was harvested after 24 hours and stored at 4° C. before purification. Vegetative cells were disrupted by heat treatment at 65° C. Purification entailed repeated washing steps using sterile deionised water with centrifugation at 5000×g for 20 min. Spores were enumerated using an improved Neubauer counting chamber and viable spore count was assessed by colony forming units on RC agar.

The capacity of CHN-1 spores to germinate and grow in the colon environment was assessed using a simulation of the proximal large intestine as described by Molly et al., (1993) *Appl Microbiol Biotechnol*. Pre-reduced sugar-depleted base colon medium containing nutrients that are present in the colon (e.g. host or diet derived glycans such as mucin or starch) was added to double-jacketed glass bioreactors. CHN-1 spores and/or faecal inoculum were added to bioreactors inside the anaerobic workstation. The faecal inoculum was prepared from faecal donor material of a single healthy donor by mixing fresh faecal sample 1:5 with pre-reduced phosphate buffer and removal of particles by centrifugation at 500×g. The inoculum was then added to the bioreactor at dilution of 1:10. Bioreactors were sealed with rubber stoppers to maintain anaerobiosis.

The experiment entailed 4 different conditions in triplicate: i) inoculation with filter-sterilized faecal suspension and CHN-1; ii) inoculation with filter-sterilized faecal suspension, CHN-1 and glucose (1 g/L); iii) inoculation with faecal suspension and CHN-1; and iv) inoculation with faecal suspension. Bioreactors were maintained at 37° C. and continuous mixing was applied at 90 rpm. Samples were removed for analysis at t=0, 2, 4, 6, 24, 30, and 48 hours after inoculation.

Germination of spores, growth and metabolic activity of CHN-1 was assessed by 1) colony forming units on selective medium; 2) pH decrease; 3) SCFA production; and 4) production of (R)-3-HB. 5) Detection of CHN-1 was performed using two specific PCR protocols for detection of *C. butyricum* 16s-23s intergenic spacer region and detection of phaB.

1) Colony forming units were assessed on modified *C. butyricum* isolation medium (BIM) as described by Popoff (1984) *J Clin Microbiol*, using D-Cycloserine as sole antibiotic agent at a concentration of 250 μg/mL. This medium allowed for the selective enumeration of CHN-1 with no colonies being observed in background without supplementation of this strain (detection threshold 200 CFU/mL). Total viable counts (FIG. 7) were assessed by serially diluting samples and plating onto modified BIM. Colony forming units were enumerated after overnight incubation in anaerobic conditions. Heat-resistant counts (FIG. 8) were assessed by pasteurizing samples for 30 min at 65° C. before serially diluting and plating onto modified BIM. Colony forming units were enumerated after overnight incubation in anaerobic conditions.

Figure 7:
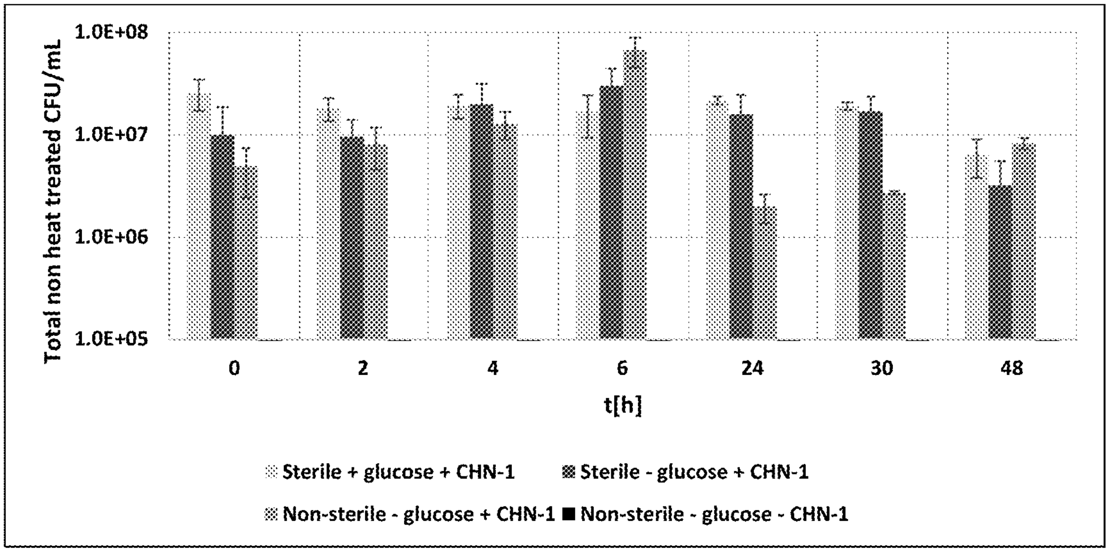
FIG. 7 shows total viable counts of CHN-1 on modified BIM expressed as colony forming units/mL. CFU/mL are shown as the mean of three independent experiments with error bars representing standard deviation.

As shown in FIG. 7, there was no significant difference between the total viable count enumerated from reactors inoculated with filter-sterilized faecal suspension and CHN-1 with or without glucose. In bioreactors inoculated with CHN-1 and faecal suspension there was a steady increase of total viable count for the first 6 hours of the experiment, indicating germination and growth of CHN-1. There was a statistically significant higher number of total viable count of CHN-1 in bioreactors inoculated with filter-sterilized faecal suspensions compared to those inoculated with faecal suspension after 24 hours ($p<0.05$), indicating that there was competition between the faecal microbiota and CHN-1 in those bioreactors. The bioreactors not inoculated with CHN-1 did not return any CFU above the detection threshold.

Figure 8:
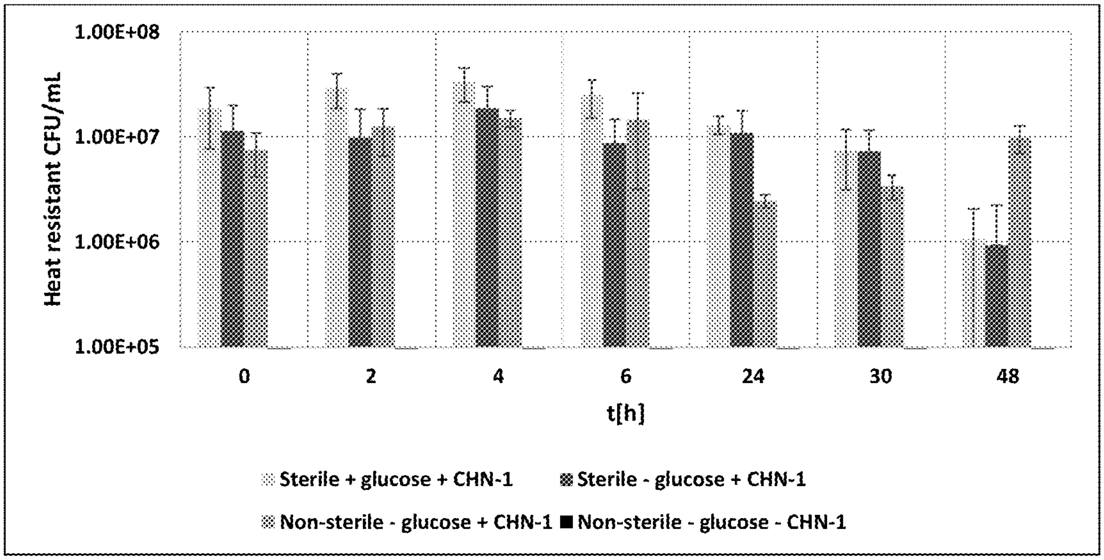
FIG. 8 shows heat-resistant counts on modified BIM expressed as colony forming units/mL. CFU/mL are shown as the mean of three independent experiments with error bars representing standard deviation.

As shown in FIG. 8, there was no significant difference in heat-resistant count enumerated from bioreactors inoculated with filter-sterilized faecal suspension and CHN-1 with or without glucose. There was a steady decrease in heat-resistant count in all bioreactors between 4 and 24 hours of incubation, indicating the germination and outgrowth from spores leading to vegetative cell growth.

2) The decrease in pH (FIG. 9) caused by metabolic activity within the colonic simulation was measured at t=0, 6, 24, and 48 hours using a Senseline F410 pH meter (ProSense, Oosterhout, NL).

Figure 9:
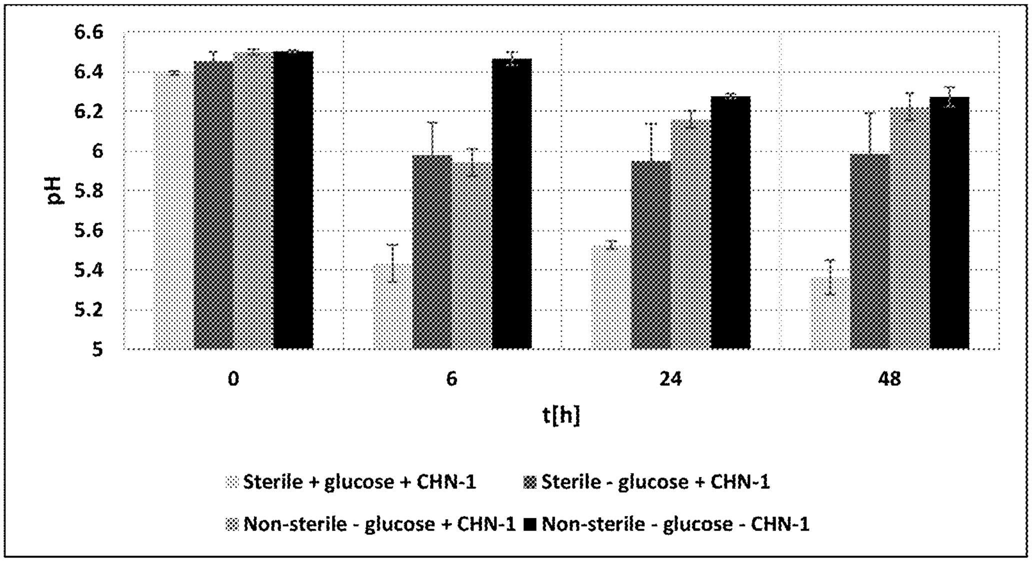
FIG. 9 shows pH within colonic simulation measured at different time points.

As shown in FIG. 9, there was no significant difference in the pH of the four experimental set-ups at the start of the experiment. Nor was there a significant difference in the pH of the bioreactors inoculated with filter-sterilized faecal inoculum and CHN-1, and the bioreactors seeded with faecal suspension and CHN-1 at any time during the experiment. There was, however, statistically significant difference in pH of the bioreactors inoculated with filter-sterilized faecal suspension and CHN-1 when comparing those with added glucose to those without from time point 6 hours onwards ($p<0.02$). There was also statistically significant difference between the bioreactors inoculated with faecal suspensions when comparing those with addition of CHN-1 and those without at time points 6 hours and 24 hours ($p=0.003$ and 0.0133, respectively). This indicates that CHN-1 is metabolically active in each of the respective backgrounds, with filter-sterilized faecal suspension and with faecal suspension within the first 6 hours of instillation.

3) The production of SCFA acetate (FIG. 10), and butyrate (FIG. 11) was measured by gas chromatography as described by De Weirdt et al. (2010) *FEMS Microbiol Ecol*.

Figure 10:
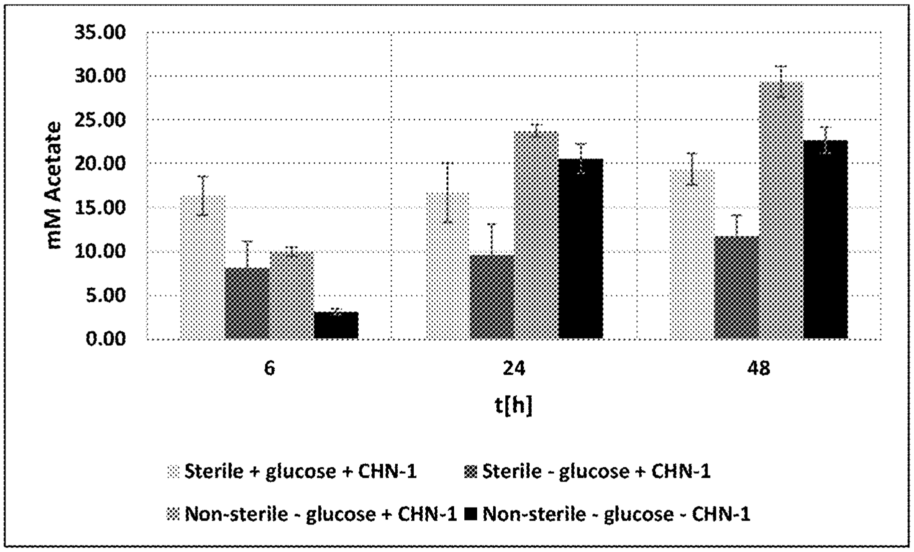
FIG. 10 shows the presence of acetate (mM) in colonic simulation at selected time-points.

As shown in FIG. 10, there was a statistically significant increase in acetate concentration in bioreactors dosed with faecal inoculum and CHN-1 compared to those inoculated with faecal inoculum only after 6 hours of incubation until the end of the experiment ($p<0.04$). There was also a significantly higher amount of acetate in the bioreactors containing faecal inoculum and CHN-1 compared to those containing filter-sterilized faecal suspension and CHN-1 from time point 24 hours onwards ($p<0.003$).

Figure 11:
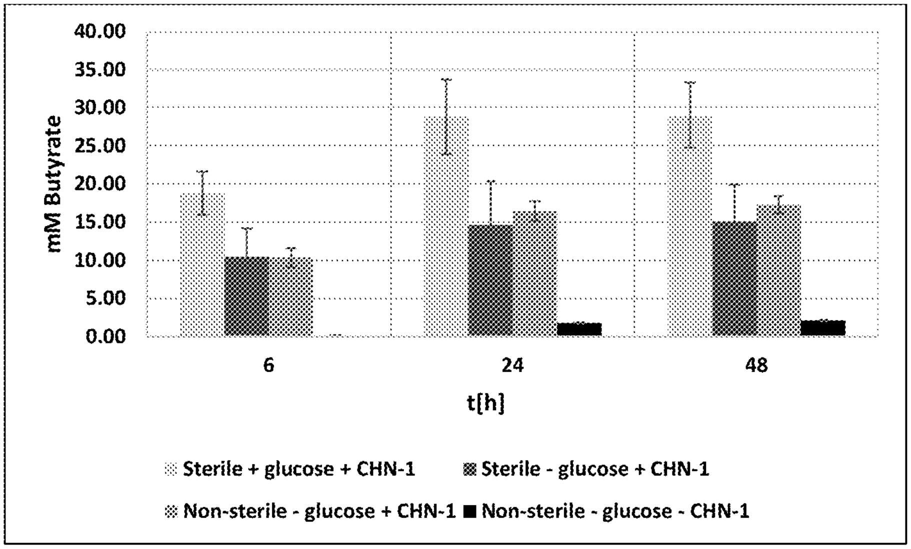
FIG. 11 shows the presence of butyrate (mM) in colonic simulation at selected time-points.

As shown in FIG. 11, there was a statistically significant increase in butyrate concentration in bioreactors dosed with faecal inoculum and CHN-1 compared to those dosed with faecal suspension only throughout the experiment ($p=0.0001$). There was no significant difference between the bioreactors containing CHN-1 with or without faecal suspension. The highest amount of butyrate was found in those reactors, where glucose had been supplemented as a precursor of butyrate production ($p<0.04$).

4) The production of (R)-3-HB in the colonic simulation was measured by HPLC-RI using an Aminex HPX-87H column of 300 mm×7.8 mm with 9 μm particle size (Biorad, USA) on a Dionex UltiMate 3000 System (Thermo Scientific, USA) set to 35° C. and a run time of 55 min. As mobile phase, 5 mM $H_2SO_4$ with a flow rate of 0.5 mL/min was used. Culture samples were filter-sterilized prior to analysis using KX syringe filters of 13 mm diameter with regular cellulose of pore size 0.22 μm (Kinesis Ltd, UK). A known amount of (R)-3-HB was spiked into samples before samples were mixed 1:1 with mobile phase containing 50 mM valerate as internal standard. Calibration standards containing increasing concentrations of glucose, (R)-3-HB, butyrate, acetate, and lactate were run at the same time as the spiked samples.

Figure 12A:
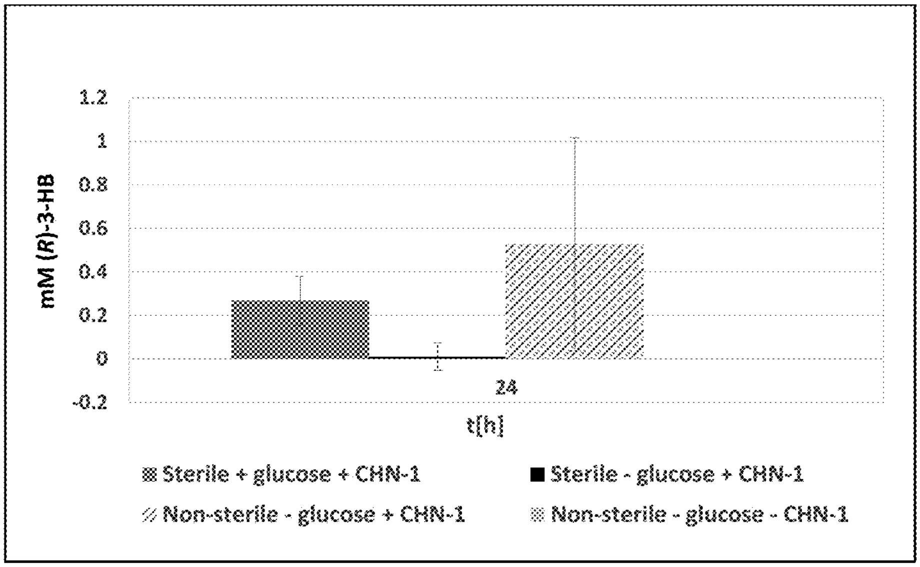
FIG. 12 shows the production of (R)-3-HB in colonic simulation at 24 hours for combined experimental replicates (A) and for each experimental replicate (B).

As shown in FIG. 12A, there was a significantly higher amount of (R)-3-HB produced in the bioreactor inoculated with filter-sterilized faecal suspension, CHN-1 and glucose in comparison to the bioreactor without glucose. There was a significantly higher amount of (R)-3-HB present in any bioreactor dosed with CHN-1 compared to those dosed with faecal suspension only ($p<0.03$). This indicates the production of (R)-3-HB in all bioreactors is dependent on the presence of CHN-1.

Figure 12B:
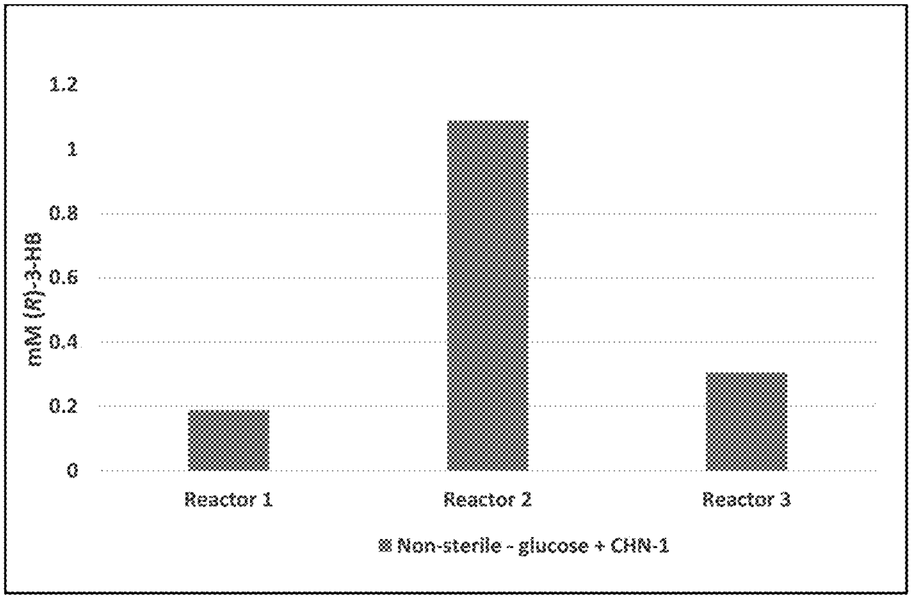

FIG. 12B shows the (R)-3-HB concentrations measured for each of the three experimental replicates conducted for the third experimental condition (inoculation with faecal suspension and CHN-1) of FIG. 12A. These three values are combined and represented in FIG. 12A. (R)-3-HB was detected in all three replicates above the baseline concentrations found in human blood serum (0-200 μM) under fed conditions. One reactor showed levels at around 1 mM. This range of 200 μM-1 mM (R)-3-HB was found to be effective at reducing the expression of multiple inflammatory proteins and increasing the expression of anti-inflammatory proteins in two human colon tissue based in vitro models, as described in Examples 5 and 6.

5) The presence of CHN-1 in the bioreactors was further confirmed using strain-specific PCR. For this, two different sets of oligonucleotides were used (table 1). One set amplified the 16s-23s intergenic spacer region of *C. butyricum* as described by Nakanishi et al. (2005) *Microbiol Immunol.* The second set specifically amplified the integrated phaB gene.

TABLE 1

| Oligonucleotide sequences | | |
|---|---|---|
| Name | Sequence | SEQ ID NO. |
| ISR-F | CCTCCTTTCTATGGAGAAATCTAGCA | 2 |
| ISR-R | TGTAGCTTGACCTTTTTAAGTTTTGA | 3 |
| phaB-F | GTGTAGTAGCCTGTGAAATAAG | 4 |
| phaB-R | GAGGCACATTTATTTTAGCTAGCTTACTAACCCATGTG | 5 |

Genomic DNA was extracted using phenol-chloroform extraction before subjected to PCR using both oligonucleotide sets.

Figure 13:
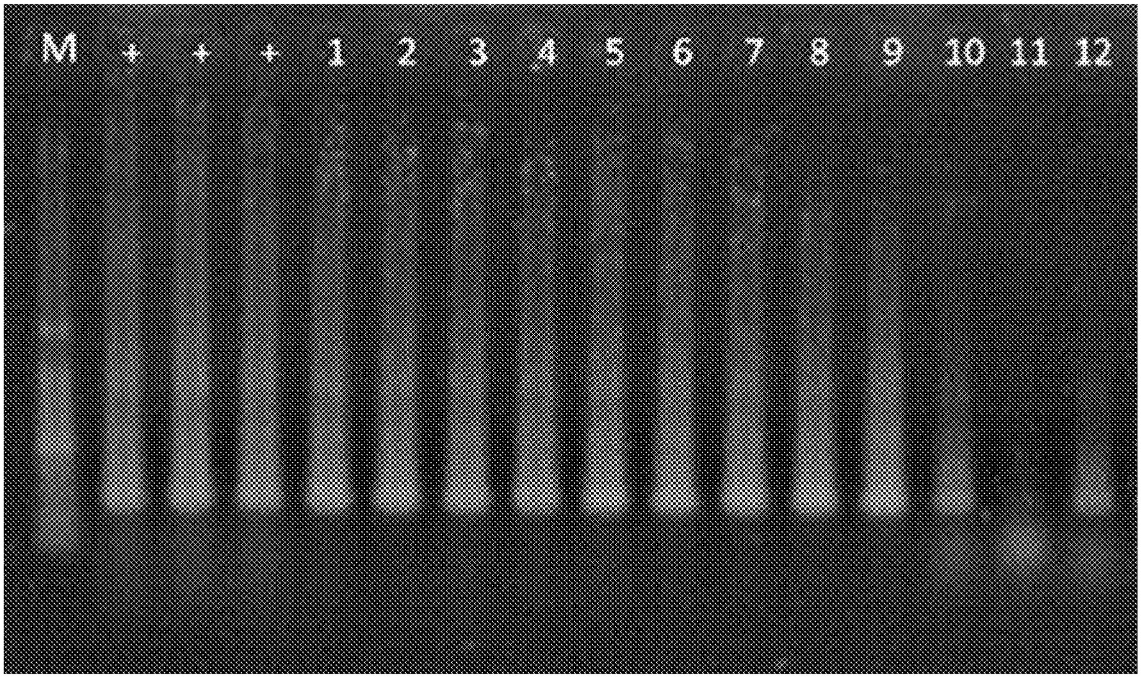
FIG. 13 shows 16s-23s intergenic spacer region-specific PCR using oligonucleotide ISR-F and ISR-R to detect CHN-1 in bioreactors.

As shown in FIG. 13, the presence of *C. butyricum* was confirmed in samples 1-9, corresponding to bioreactors dosed with CHN-1 spores. Low levels of *C. butyricum* (below detection level in total viable count and heat-resistant count (FIGS. 7 and 8)) were also confirmed in reactors 10-12, which were dosed with faecal suspension only.

Figure 14:
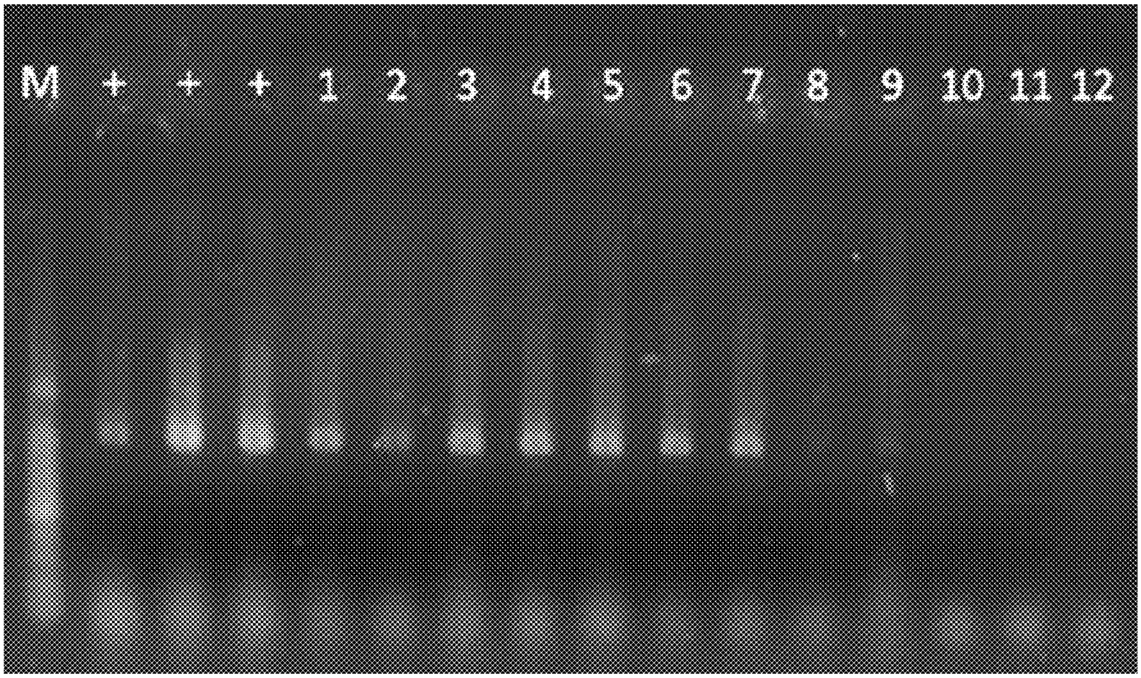
FIG. 14 shows phaB specific PCR using oligonucleotide phaB-F and phaB-R to detect CHN-1 in bioreactors.

As shown in FIG. 14, the presence of phaB was confirmed in samples 1-9, corresponding to bioreactors dosed with CHN-1 spores. No amplicon was observed in reactors dosed with faecal suspension only, confirming absence of phaB in these bioreactors.

In summary, these data show that CHN-1 spores can germinate in the simulated colonic environment. Germination of these spores subsequently leads to vegetative cell growth as shown by indicators of metabolic activity, here SCFA concentration and pH drop. The data also shows that CHN-1 successfully introduces a new metabolic product, namely (R)-3-HB, which is not normally found in the colonic environment.

Example 5—Modelling Inflammation Using Primary Human Intestinal Organoids

To measure the effect of (R)-3-HB on inflammation of primary human intestinal organoids, healthy large intestine samples of a female 67-year old donor were cultured for 8 weeks in vitro prior to experiments. Method as used in Hannan et al., Stem Cell Reports. Vol. 1, 293-306 Oct. 15, 2013.

1) To induce inflammation, organoids were treated with TNFα (40 ng/mL) alone or in combination with butyrate (10 μM), (R)-3-HB (10 μM), or butyrate and (R)-3-HB for 18 hours. Subsequently, cells were lysed and RNA was isolated for cDNA synthesis and measurement of mRNA expression levels of inflammation factors, NF-κB and TNFα, by qPCR.

Figure 15A:
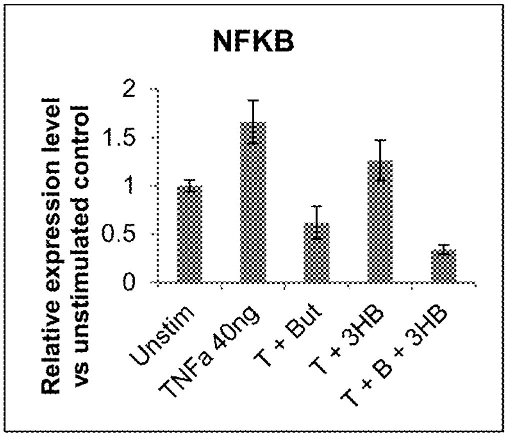
FIG. 15 shows data from an intestinal organoid model. Relative expression (mRNA) levels, versus unstimulated organoids, of inflammatory factors NF-κB (A) and TNFα (B) are provided when organoids are incubated with TNFα, TNFα and butyrate and/or (R)-3-HB.
Figure 15B:
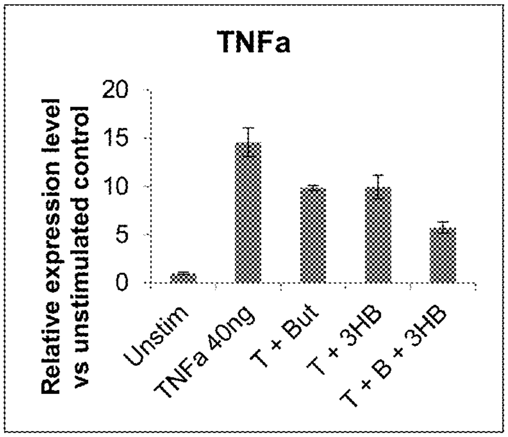
Figure 16A:
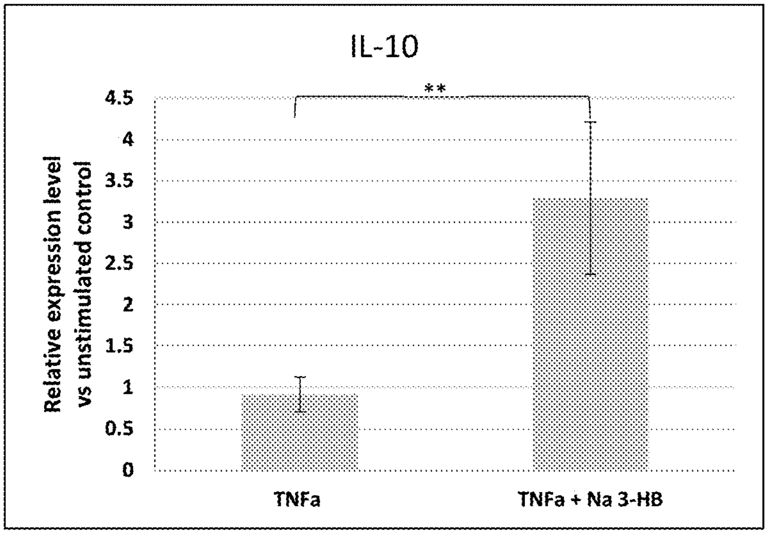
FIG. 16 shows data from an intestinal organoid model. Relative expression (mRNA), versus unstimulated organoids, for inflammatory markers IL-10 (A), IL-23 (B), TNF-α (C), IL-1β (D), TGF-β1 (E), IL-6 (F) and NF-κβ (G) is shown when organoids are stimulated with TNF-α alone or together with (R)-3-HB.
Figure 16B:
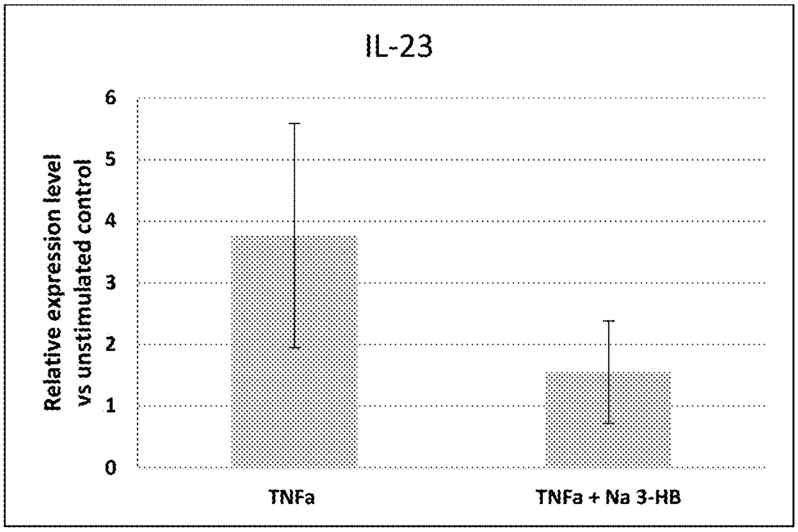
Figure 16C:
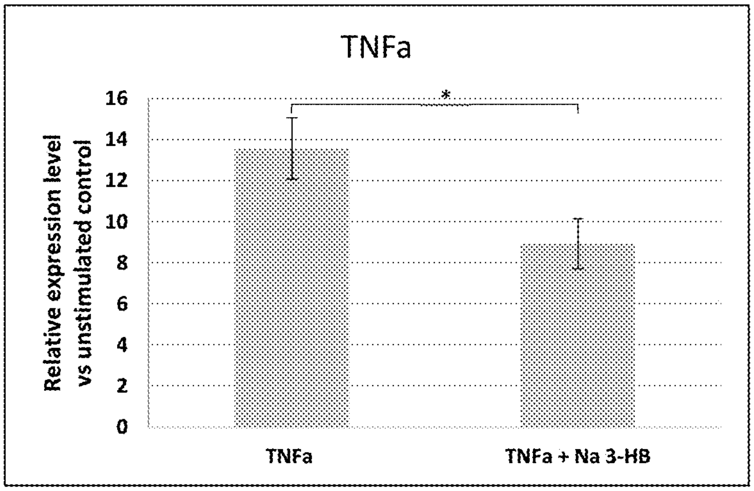
Figure 16D:
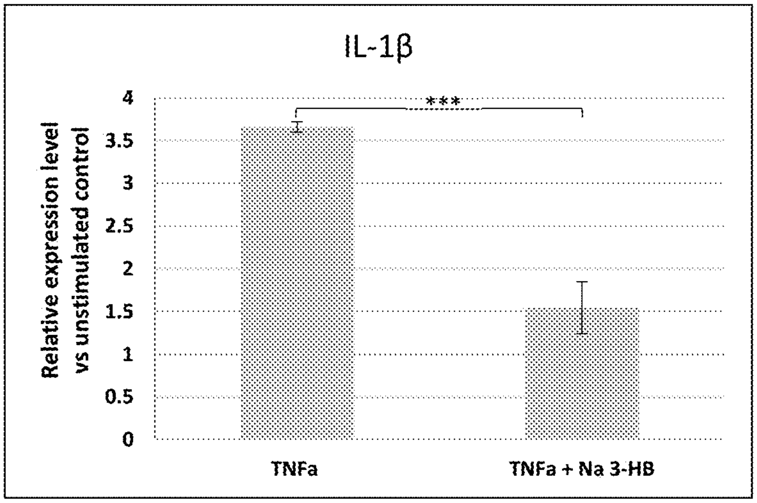
Figure 16E:
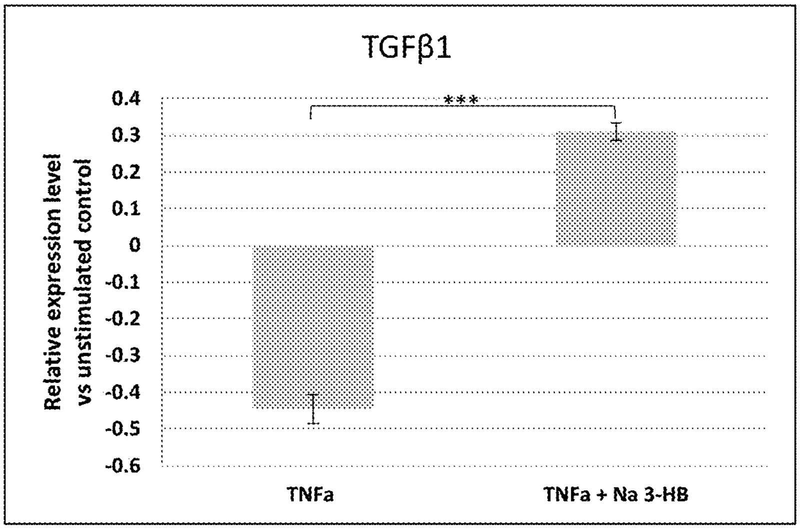
Figure 16F:
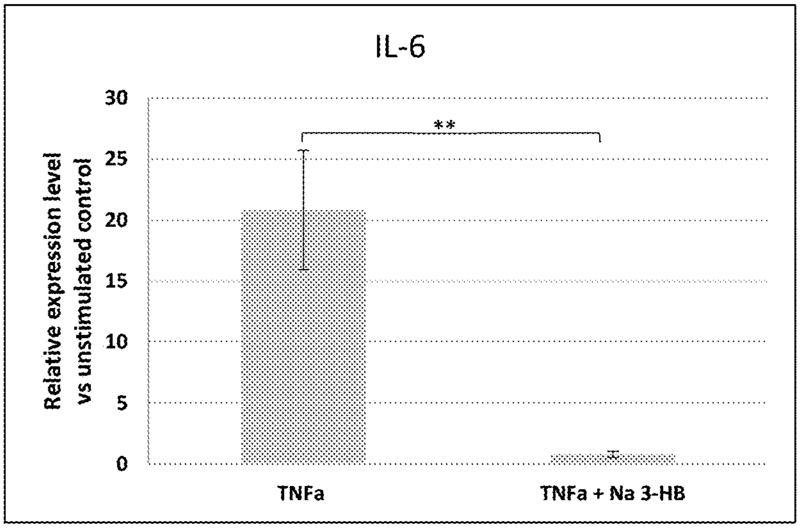
Figure 16G:
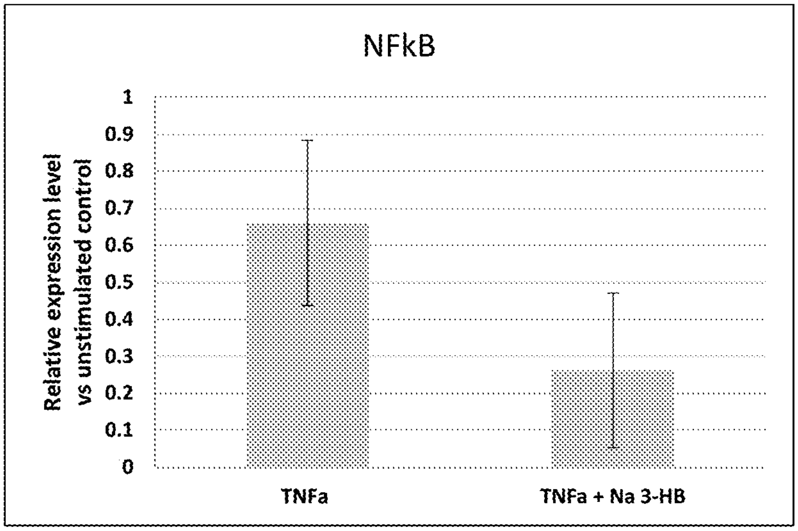

FIG. 15 shows the relative mRNA expression levels, as standardised against the control (unstimulated sample) set to 1, of inflammatory factors, NF-κB (A) and TNFα (B) expressed by primary human intestinal organoids in response to incubation with TNFα in combination with butyrate, (R)-3-HB, or a combination of butyrate with (R)-3-HB. The mRNA expression of the inflammation factors NF-κB and TNF-α decreased with treatment with butyrate, (R)-3-HB, or a combination of butyrate and (R)-3-HB.

2) To induce inflammation, organoids were treated with TNF-α (40 ng/mL) alone or in combination with (R)-3-HB (sodium salts at 10 μM) for 18 hours. Subsequently, cells were lysed and RNA was isolated for cDNA synthesis and mRNA expression levels of a panel of inflammation factors was measured by qPCR.

FIG. 16 shows the relative mRNA expression levels, as standardised against the normalized control (unstimulated sample set to 0), of inflammatory factors, expressed by primary human intestinal organoids in response to incubation with TNF-α alone or in combination with (R)-3-HB. The mRNA expression of pro-inflammatory cytokines and proteins IL-23, TNF-α, IL-10, IL-6 and NF-κβ decreased in the presence of (R)-3-HB compared to treatment with TNF-α alone. The mRNA expression of anti-inflammatory cytokines TGF-β1 and IL-10 increased in the presence of (R)-3-HB compared to treatment with TNF-α alone.

Both butyrate and (R)-3-HB act on pro-inflammatory cytokines and proteins and anti-inflammatory cytokines and proteins. (R)-3-HB has greater reducing effect than butyrate on multiple important pro-inflammatory regulators of IBD and greater inducing effect on major protective regulators of intestinal inflammation (data not shown).

3) The effect of (R)-3-HB and the related SCFA butyrate on the inflammatory response exerted by primary human intestinal organoids upon co-incubation with TNF-α as inflammatory stimulus was measured. Primary human intestinal organoids were cultured for 8 weeks prior to experiments as described in Hannan et al. (2013) Stem Cell Reports.

To induce inflammation, organoids were treated with 60 ng/mL TNF-α alone or in combination with different concentrations of the sodium salts of (R)-3-HB or butyrate for 24 hours. Subsequently, cells were lysed and RNA was isolated using the RNeasy mini kit (Qiagen Ltd, Germany) for synthesis of cDNA. mRNA expression levels of IL-23 was measured by qPCR using the SensiMix SYBR low-ROX kit (Bioline, UK).

Values were normalized versus untreated control and graphs show the difference of mRNA levels measured in organoids treated with TNF-α alone (set as 0) and those treated with TNF-α and butyrate or (R)-3-HB.

Figure 17:
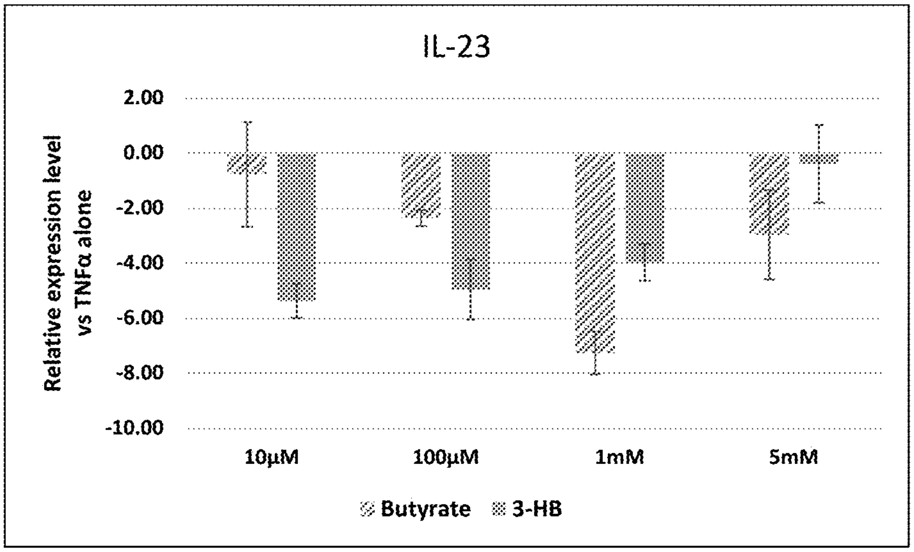
FIG. 17 shows relative mRNA expression level of IL-23 in organoids treated with 60 ng/mL TNF-α and increasing concentrations of butyrate or (R)-3-HB.
Figure 18A:
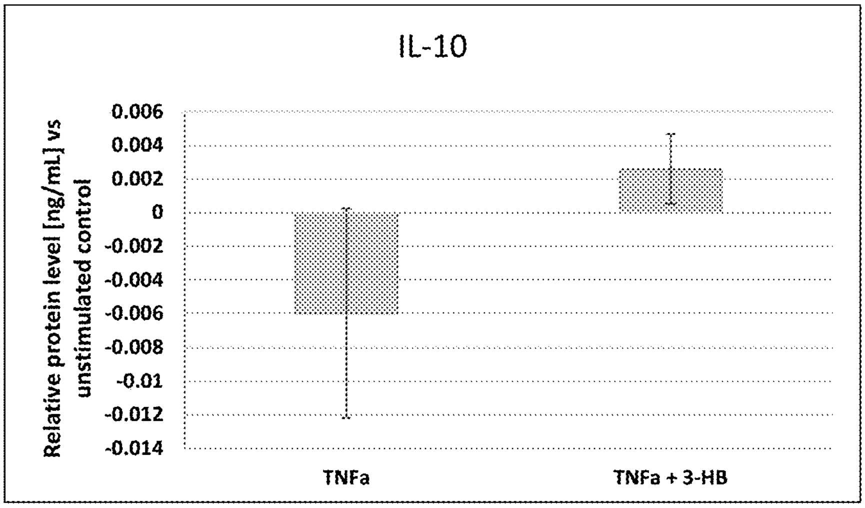
FIG. 18 shows data from an ex-vivo tissue model. Relative protein amount (Luminex), versus unstimulated tissue samples, for inflammatory markers IL-10 (A), IL-12 (B), IL-1β (C) and IL-6 (D) is shown when ex-vivo colon tissue samples are stimulated with TNF-α alone or together with (R)-3-HB.
Figure 18B:
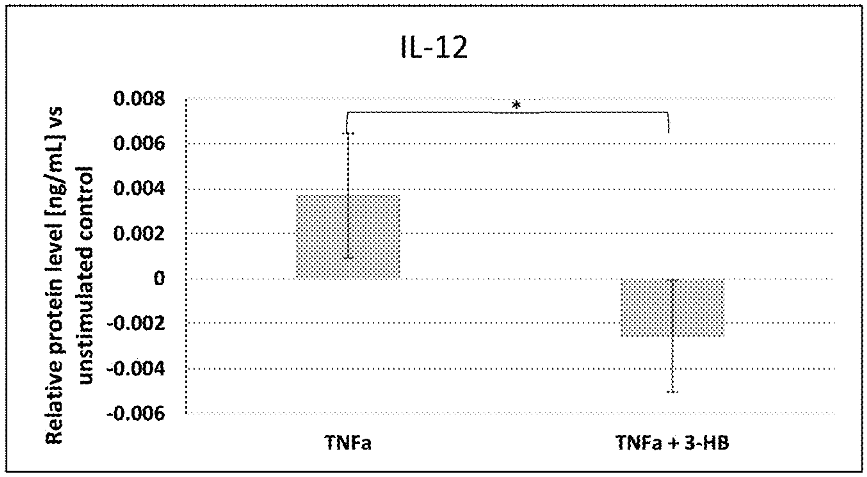
Figure 18C:
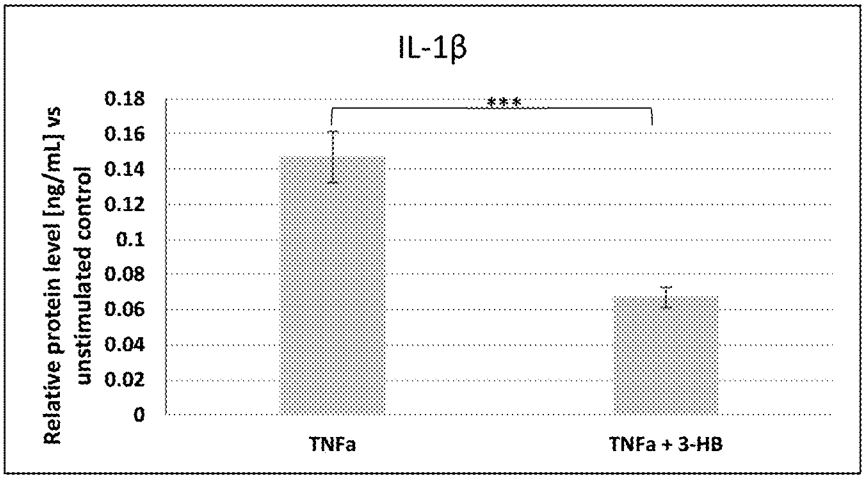
Figure 18D:
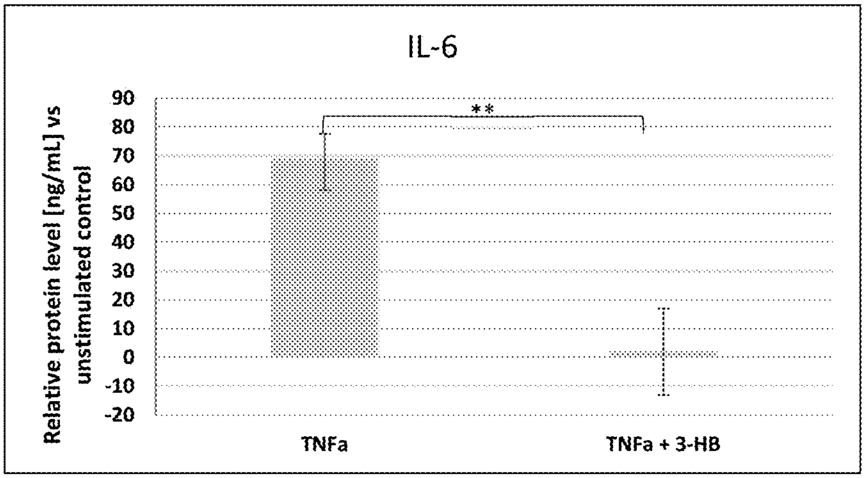

FIG. 17 shows the relative mRNA expression level of IL-23 in organoids treated with 60 ng/mL TNF-α and increasing concentrations of butyrate or (R)-3-HB. These data indicate that 10-100 μM concentrations of (R)-3HB may be effective at reducing expression of IL-23 in human gut mucosa. 11-23 is a key mediator of inflammation in IBD and is the target for several pharmaceutical monoclonal antibody drugs. This concentration range of (R)-3-Hb is achievable in the gut lumen using bacterial delivery as evidenced by in vitro gut modelling. (See FIG. 12). (R)-3-HB has a greater reducing impact on IL-23 expression at these concentrations than Butyrate.

Example 6—Modelling Inflammation Using an Ex-Vivo Human Colon Tissue Model

Colorectal specimens can be obtained from surgical resections of intestinal tissue or from biopsies, after receiving signed informed consent from the patients.

Materials:

Specimen collection pots, Sterile scalpels, Sterile forceps, Petri plates, PBS, Dulbecco's Minimal Essential Medium (DMEM) high glucose, Fetal calf serum (FCS), L-glutamine, antibiotics, 96-well U-bottom sterile plates with lid, Multi-channel pipettor.

Preparations of Colorectal Explants.

Following resection of tissue, specimens are kept in a specimen collection pot containing DMEM for transportation to the laboratory. Put the specimen in a Petri plate with some medium. Strip the muscle from the resected specimen with sterile scalpel. Transfer the remaining tissue into a new Petri plate with medium and cut the tissue into explants comprising both epithelial and muscularis mucosae (Berry N, Herrera C, Cranage M. Methods Mol. Biol. 2011; 665: 133-60). Proceed to assay.

Pre-Clinical Evaluation of Candidate Compounds.

To induce inflammation, explants are incubated with 100 μl of inflammatory stimulus (TNF-α 15 μg/ml) in 96-well U-bottom sterile plates. Incubate explants for one hour with 100 ml of complete medium (DMEM containing FCS, L-glutamine and antibiotics). To evaluate the activity of compounds of interest, 100 μl of compounds (10 mM) are added to explants. Tissue explants are then cultured at 37° C. in an atmosphere containing 5% CO2 for 24 hours. Negative controls are tissue explants cultured without stimulus nor candidate compounds (add 200 μl of complete medium). Positive controls are explants treated only with inflammatory stimulus. Following culture, remove tissue explants from culture wells, spin down plates and harvest 180 μl of the culture supernatant. Freeze supernatants and tissue explants at −80° C. Proceed to quantification of analytes of interest in supernatants and/or tissue explants.

The Luminex method was used to determine protein concentration in culture supernatants: Luminex Protocol: In house assay was conducted by Dr Carolina Herrera at St Mary's Hospital, Paddington, London. Luminex Assay Buffer: PBS, goat serum, mouse serum, Tween 20, Tris pH 7-8. Luminex Wash Buffer: PBS, Tween-20. Procedure:

Prepare the Assay Plate

1. Prewet the assay plate with assay buffer

Prepare the Standards

1. Prepare 11 standards with dilution steps of 1/3

Prepare the Samples

1. Dilute samples as required per panel

Prepare the Beads

1. Sonicate and vortex beads
2. Dilute beads in assay buffer

Set Up the Assay

1. Remove assay buffer from the plate
2. Add 50 μl of standards, blank and samples to corresponding wells
3. Add 50 μl of bead mix into each well
4. Cover plate with foil and shake for 1 h 30 min on plate shaker Add Detection Antibody Cocktail 1. Dilute detection antibody cocktail in assay buffer
2. Wash plates 3× with wash buffer
3. Add 50 μl detection antibody cocktail per well
4. Cover with foil and shake for 1 hour as before Add Streptavidin-PE 1. Dilute Streptavidin-PE in assay buffer
2. Wash plate 3× with wash buffer
3. Add 50 μl of diluted Streptavidin-PE to each well
4. Cover with foil and shake for 30 minutes
5. Wash 3× and add 100 μl of sheath fluid to each well
6. Either shake before running plate through the luminex or store in the fridge, wrapped in foil until the next day.

FIG. 18 shows the relative protein levels, as standardised against the normalized control (unstimulated sample set to 0), of inflammatory factors, expressed by ex vivo colon tissue samples, in response to incubation with TNF-α alone (60 min) or TNF-α (60 mins) followed by exposure to (R)-3-HB (24 hours). Both the sodium salts for 3-hydroxybutyric acid and the pure acids were investigated, all at 10 mM concentration. Relative protein level [ng/mL] was determined using a standard curve. The protein concentration of pro-inflammatory cytokines and proteins IL-12, IL-1β and IL-6 decreased in the presence of (R)-3-HB compared to treatment with TNF-α alone. The protein concentration of the anti-inflammatory cytokine IL-10 increased in the presence of (R)-3-HB compared to treatment with TNF-α alone. Both butyrate and (R)-3-HB act on pro-inflammatory cytokines and proteins and anti-inflammatory cytokines and proteins. (R)-3-HB has greater reducing effect than butyrate on multiple important pro-inflammatory regulators of IBD and greater inducing effect on major protective regulators of intestinal inflammation (data not shown).

A Proteome Profiler™ Array was used to measure the relative abundance of a larger set of proteins and cytokines involved in the immune response. The experimental conditions and the preparation of the colon tissue samples was the same as described above. The Human XL Cytokine Array Kit (www.rndsystems.com), Catalog Number ARY022 was used for this experiment. Cytokines, chemokines and growth factors are extracellular signaling molecules that mediate cell to cell communication. These molecules are released from cells and have critical roles in many biological processes such as cellular growth, differentiation, gene expression, migration, immunity and inflammation. In most biological processes, multiple cytokines operate in a large network, where the action of one cytokine is regulated by the presence or absence of other cytokines. The Human XL Cytokine Array Kit is a rapid, sensitive, and economic tool to simultaneously detect cytokine differences between samples. The relative expression levels of 102 human soluble proteins can be determined without performing numerous immunoassays.

Principle of the Assay

Capture and control antibodies have been spotted in duplicate on nitrocellulose membranes. Cell culture supernates, cell lysates, serum, plasma, human milk, urine, saliva, or tissue lysates are diluted and incubated overnight with the Proteome Profiler Human XL Cytokine Array. The membrane is washed to remove unbound material followed by incubation with a cocktail of biotinylated detection antibodies. Streptavidin-HRP and chemiluminescent detection reagents are then applied, and a signal is produced at each capture spot corresponding to the amount of protein bound.

Figure 19A:
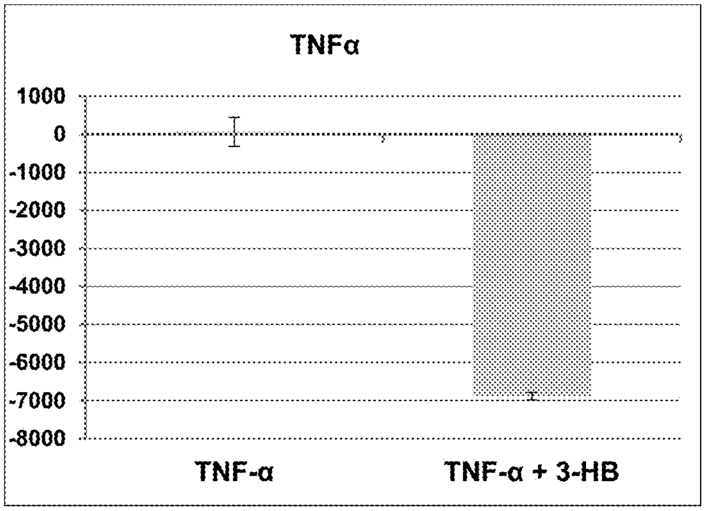
FIG. 19 shows data from an ex-vivo tissue model. A comparative Proteome Dot Blot Array experiment was used to compare protein expression levels in ex-vivo colon tissue samples that are stimulated with TNF-α alone or together with (R)-3-HB. Data for the inflammatory markers TNF-α (A), IL-23 (B) and MMP9 (C) are shown.
Figure 19B:
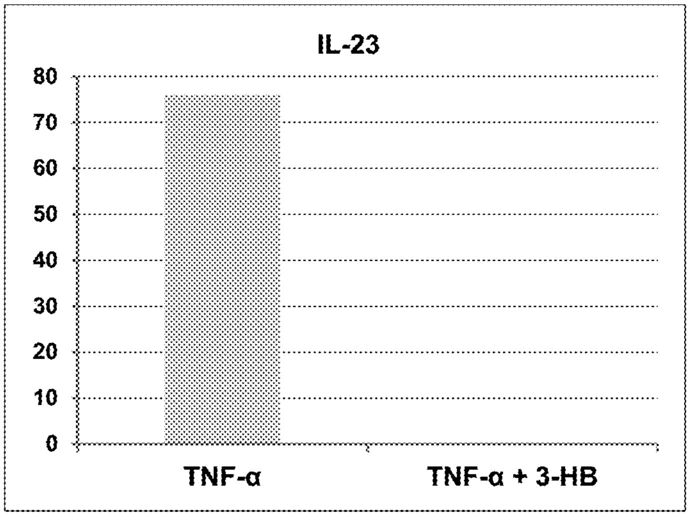
Figure 19C:
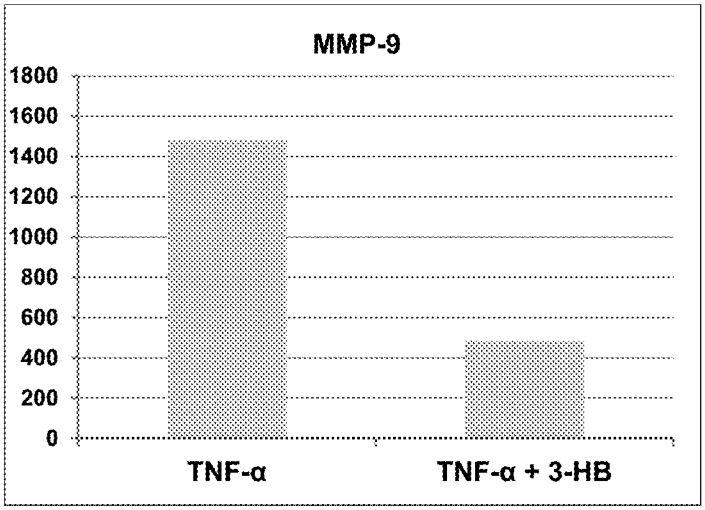

FIG. 19 shows the relative protein abundance (non-quantitative), as standardised against the normalized control (unstimulated sample set to 0), of inflammatory factors, expressed by ex vivo colon tissue samples, in response to incubation with TNF-α alone (60 min) or TNF-α (60 mins) followed by exposure to (R)-3-HB (24 hours). Both the sodium salts for 3-hydroxybutyric acid and the pure acids were investigated, all at 10 mM concentration. The protein concentration of pro-inflammatory cytokines and proteins TNF-α, IL-23 and MMP9 decreased in the presence of (R)-3-HB compared to treatment with TNF-α alone.

Example 7—Germination and Outgrowth Competition Assay

Spores of *C. difficile* and genetically engineered *C. butyricum* were obtained by harvesting spore stocks from rich medium plates after 5 days of incubation. Samples were heat-treated at 65° C. for 30 min to kill any remaining vegetative cells. To germinate spores, 50 μL of spore cultures were inoculated into 10 mL of rich medium supplemented with 0.1% sodium taurocholate (inducer of *C. difficile* germination). Spores of *C. difficile* and *C. butyricum* were used in single and in co-culture in triplicate experiments. After incubating for 24 h in anaerobic conditions at 37° C., samples were taken from each individual experiment, serially diluted and plated in 20 μL discreet spots in triplicate on rich medium. After incubation overnight at 37° C. anaerobically, CFU/mL were determined.

Figure 20:
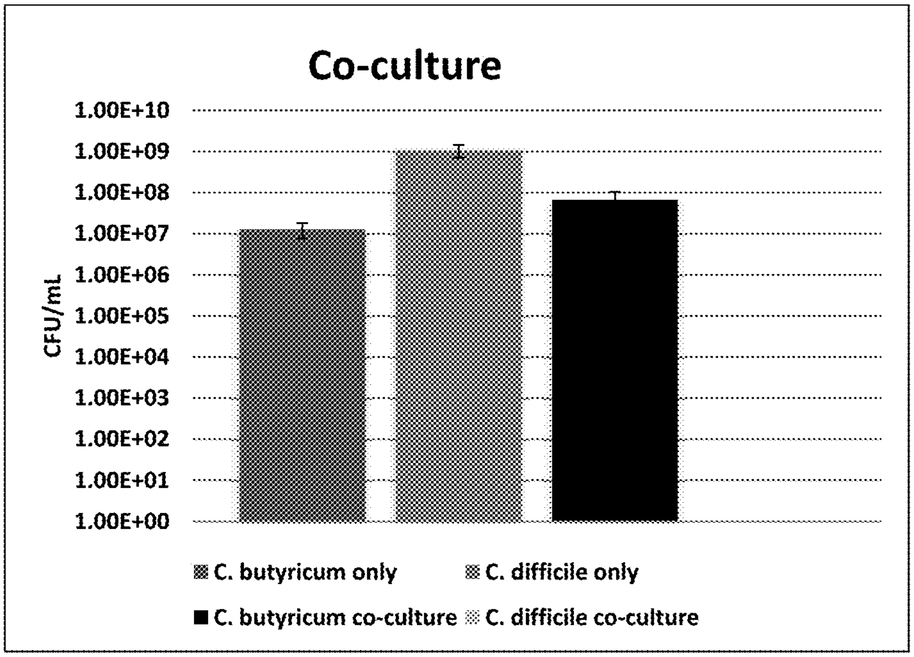
FIG. 20 shows CFU/mL obtained by germination and outgrowth of spores of *C. butyricum* and *C. difficile* in single and co-culture.

FIG. 20 shows the CFU/mL obtained by single and co-culture of spores of *C. difficile* and *C. butyricum*. Germination and/or outgrowth of *C. difficile* was completely inhibited when spores were germinated co-cultured alongside spores of *C. butyricum.*

Example 8—Evaluation of Survival in Stomach and Small Intestine Conditions

Spores of CHN-1 were resuspended in 1 mL PBS and inoculated into 9 mL of Gastric simulation medium (GSM) containing in g/L: arabinogalactan, 1, pectin, 2, xylan, 1, starch, 3, glucose, 0.4, yeast extract, 3, peptone, 1, mucin, 4, cysteine, 0.5, and pepsin, 1. The medium was adjusted to pH3 before autoclaving using 1M HCl. The GSM cultures were incubated anaerobically at 37° C. with 100 rpm agitation for 2 hours, before addition of 5 mL of pre-reduced pancreatic bile fluid containing in g/L: pancreatin, 3, dehydrated bile extract, 8, sodium bicarbonate, 10. Cultures were incubated anaerobically at 37° C. with 50 rpm agitation for 4 hours. The GSM was not prereduced but stored at 37° C. before transfer to the cabinet to mimic oxic conditions encountered in the stomach and reduction of oxygen encountered by travel through the gastrointestinal tract by subsequent anaerobic incubation. Samples were taken at t=0, 2, 4, and 6 hours of incubation. Samples were serially diluted and spotted in 3 discreet 20 μL spots onto RCM agar plates. Plates were incubated anaerobically at 37° C. overnight before colony count to assess viability of spores in stomach and small intestine conditions.

Figure 21:
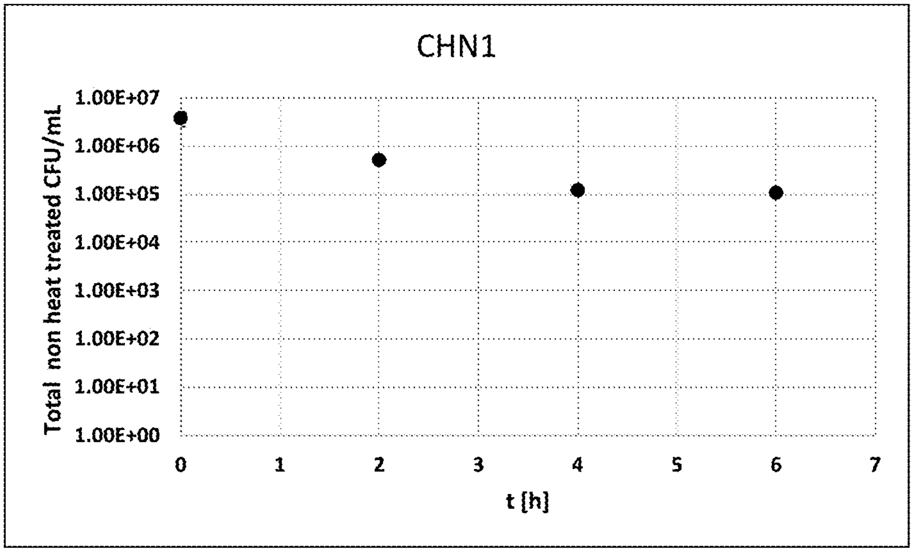
FIG. 21 shows colony forming units per mL of spores of CHN-1 on RCM agar plates after incubation in stomach and small intestine conditions. Data points represent the mean of three independent experiments with error bars showing the standard deviation.

FIG. 21 shows that spores of CHN-1 survive stomach acid conditions and are then viable.

The invention claimed is:

1. A composition comprising genetically engineered anaerobic bacteria that produce 3-hydroxybutyrate (3-HB), and an orally ingestible solid carrier, for delivering 3-HB to the lumen of the GI tract.

2. A composition according to claim 1, wherein the bacteria comprise a non-native gene capable of expressing (R)-3-hydroxybutyryl-CoA dehydrogenase.

3. A composition according to claim 1, wherein the bacteria are Clostridia bacteria, bacteria from cluster I, IV and/or XIVa of Clostridia, bacteria from the *Clostridium* genus or *Clostridium butyricum.*

4. A composition according to claim 1, wherein the bacteria have native genes encoding phosphotransbutyrylase and/or butyrate kinase.

5. A composition according to claim 1, wherein the bacteria produce (R)-3-hydroxybutyrate as the sole fermentation product or produce (R)-3-hydroxybutyrate in combination with acetate and/or butyrate as fermentation products.

6. A composition according to claim 1 further comprising a pharmaceutically acceptable carrier for use as a medicament.

7. A composition according to claim 1 for use in treating an inflammatory disease; for use in treating a gastrointestinal disorder; for use in treating gastrointestinal dysbiosis; for use in treating *C. difficile* infection; for use in modulating gut flora; or for use in animal feed.

8. A composition according to claim 7, wherein the inflammatory disease or gastrointestinal disorder is inflammatory bowel disease, irritable bowel syndrome, Crohn's disease, Pouchitis, Diverticulitis, ulcerative colitis, or colon cancer.

9. A composition according to claim 1 for use in food products.

10. A composition according to claim 9, wherein the food product is a beverage, a drink a food supplement, or a nutraceutical.

11. A composition according to claim 1, wherein the genetically engineered anaerobic bacteria produce (R)-3-hyroxybutyrate ((R)-3-HB).

12. A composition according to claim 1, wherein the bacteria naturally produce butyrate.

13. A composition according to claim 6, wherein the composition delivers the 3-HB to the large intestine, an anaerobic section of the large intestine, the colon, the terminal ileum, or a combination thereof.

* * * * *

SEQUENCE LISTING

```
<160> NUMBER OF SEQ ID NOS: 5

<210> SEQ ID NO 1
<211> LENGTH: 744
<212> TYPE: DNA
<213> ORGANISM: Cupriavidus necator

<400> SEQUENCE: 1

atgactcaaa gaatagctta tgtgactgga ggaatgggtg gaataggaac tgcaatatgc     60

caaaggttag ctaaagatgg atttagagta gttgctggat gtggtccaaa ctctccaaga    120

agagaaagat ggcttgaaca gcaaaaagct ttaggttttg actttgtagc aagtgaagga    180

aacgttgctg actgggattc aactaagaca gcttttgata aagttaaagc agaagttgga    240

gaggtagatg tattaataaa taatgctgga ataactagag acgttgtttt tagaaaaatg    300

acaagagcag actgggatgc agtaattgat actaatttaa ctagcttatt taatgtgact    360

aagcaagtaa tagacggtat ggctgataga ggatggggaa gaatagtaaa tatatcaagt    420

gtaaacggtc agaaaggtca atttggacag acaaattatt caacagcaaa agctggatta    480

catggtttta ctatggcatt agcacaggaa gttgcaacaa agggagttac tgttaatact    540

gtttctccag gatatattgc aacagatatg gttaaagcaa ttagacaaga cgttttagac    600

aaaattgtag gaacaatacc tgttaaaaga cttggagagc ctgaggagat tgcaagtatt    660

tgcgcttggc tttcatctga tgaaagtggt ttttctacag gtgcagattt tagtttaaat    720

ggtggtcttc acatgggtta gtaa                                           744

<210> SEQ ID NO 2
<211> LENGTH: 26
<212> TYPE: DNA
```

-continued

```
<213> ORGANISM: Artificial Sequence
<220> FEATURE:
<223> OTHER INFORMATION: Forward primer

<400> SEQUENCE: 2

cctcctttct atggagaaat ctagca                                   26


<210> SEQ ID NO 3
<211> LENGTH: 26
<212> TYPE: DNA
<213> ORGANISM: Artificial Sequence
<220> FEATURE:
<223> OTHER INFORMATION: Reverse primer

<400> SEQUENCE: 3

tgtagcttga cctttttaag ttttga                                   26


<210> SEQ ID NO 4
<211> LENGTH: 22
<212> TYPE: DNA
<213> ORGANISM: Artificial Sequence
<220> FEATURE:
<223> OTHER INFORMATION: Forward primer

<400> SEQUENCE: 4

gtgtagtagc ctgtgaaata ag                                       22


<210> SEQ ID NO 5
<211> LENGTH: 38
<212> TYPE: DNA
<213> ORGANISM: Artificial Sequence
<220> FEATURE:
<223> OTHER INFORMATION: Reverse primer

<400> SEQUENCE: 5

gaggcacatt tattttagct agcttactaa cccatgtg                     38
```